Figure 1:
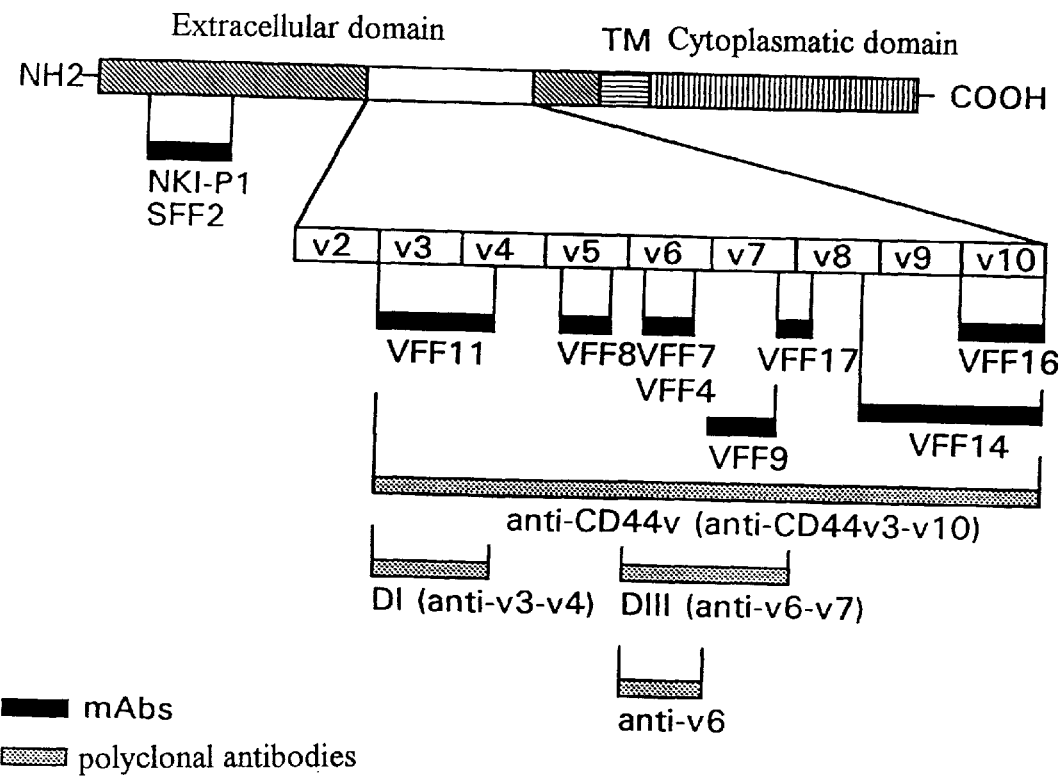

United States Patent [19]
Ponta et al.

[11] Patent Number: 6,010,865
[45] Date of Patent: Jan. 4, 2000

[54] PROCESS FOR DETECTING A VARIANT CD44 GENE PRODUCT

[75] Inventors: Helmut Ponta, Linkenheim-Hochstetten; Karl-Heinz Heider, Waldbronn-Reichenbach; Peter Herrlich, Karlsruhe, all of Germany; Steven T. Pals, Amsterdam, Netherlands; Peter Dall, Düsseldorf, Germany

[73] Assignee: Boehringer Ingelheim International GmbH, Germany

[21] Appl. No.: 08/564,225

[22] PCT Filed: Jun. 15, 1994

[86] PCT No.: PCT/EP94/01952

§ 371 Date: Jun. 3, 1996

§ 102(e) Date: Jun. 3, 1996

[87] PCT Pub. No.: WO95/00851

PCT Pub. Date: Jan. 5, 1995

[30] Foreign Application Priority Data

| Jun. 22, 1993 | [DE] | Germany | 43 20 624 |
| Jun. 22, 1993 | [DE] | Germany | 43 20 623 |
| Jul. 2, 1993 | [DE] | Germany | 43 21 944 |
| Apr. 28, 1994 | [DE] | Germany | 44 14 787 |

[51] Int. Cl.$^7$ .......................... G01J 33/53; C07H 21/02; C07K 16/00
[52] U.S. Cl. .................... 435/7.23; 536/23.1; 530/388.1; 530/388.8; 530/388.85; 530/389.1
[58] Field of Search ........................ 536/23.1; 530/388.1, 530/388.8, 388.85, 389.1; 424/130.1; 435/6, 7.1, 7.23

[56] References Cited

PUBLICATIONS

Rudzki et al (J. Clin Pathol. Mol. Pathol, 50:57–71, 1997.
Zoller (JMM, 73:425–438), 1995.
Strong in (Laboratory Diagnosis of Viral Infections, 2d Ed, E. Lennetto Ed. Marcel Dekker, Inc., NY. pp. 211–219, 1992.
Dall, et al (Cancer Res., 54:3337–3341, 1994.
Woerner et al (Clin Cancer Res, 1:1125–1132), 1995.
Woodman et al (Am. J. Pathol, 149:1519–1530, 1996.
Matsumura et al (Lancet, 340:1053–1058, 1992.
Cannistra et al (J. Clin Oncol, 13:1912–1921, 1995.
Screaton et al (PNAS, 89:12160–12164), 1992.
Tempfer et al (Cancer, 1996, 78:273–277).
Johnstone & Thorpe (Immunochemistry in Practice 2nd Ed. Blackwell Scientific Pub. Oxford, p. 30), 1987.
Huse (Science, 246:1275–1281, 1989.
Hofmann et al (Cancer Res, 51:5292–5297, 1991.
Smith et al., Alternative Splicing in the Control of Gene Expression, Annu. Rev. Genet., vol. 23:527–77 (1989).

*Primary Examiner*—Paula K. Hutzell
*Assistant Examiner*—Susan Ungar
*Attorney, Agent, or Firm*—Finnegan, Henderson, Farabow, Garrett & Dunner, L.L.P.

[57] ABSTRACT

The invention relates to a process for diagnosing and analysing tumours which is based on detecting the expression of certain variant exons of the CD44-gene. Detection may be carried out at the protein or nucleic acid level. In a preferred embodiment the expression is detected in biopsy material using exon-specific antibodies. Thus, for example, v6-expression is a suitable prognostic parameter for breast cancer, the expression of a transitional epitope which is coded by exons v7 and v8 serves to diagnose cervical cancer.

7 Claims, 16 Drawing Sheets v 3 - 1 0     v 5 / 6     v 8 - 1 0

6,010,865

PROCESS FOR DETECTING A VARIANT CD44 GENE PRODUCT

The invention relates to processes for diagnosing and/or analysing tumours by evaluating the expression of variable exons of the CD44-gene, agents for such processes and the use thereof.

There is a need for improved methods of diagnosing and/or analysing cancers, particularly on the basis of molecular markers.

For example, the haematogenic spread of mammary carcinomas occurs very early in the course of the disease and is connected with the later occurrence of remote metastases (Diel et al., 1992). The molecular mechanisms of metastatic spread are still unknown. The prognostic factors for predicting the risk of metastasis are currently based mainly on pathological criteria, the main factors being the stage of the tumour, differentiation (gradation) and lymph node metastasis (Fisher et al., 1990). However, in individual cases, there are discrepancies between these factors, e.g. where in spite of a highly advance tumour size or low differentiation (high gradation) there are no lymph node metastases. Little investigation has been carried out into a subgroup or patients suffering from lymph-node-negative breast cancer who later develop remote metastases. There is therefore a need for parameters which allow better prediction of the haematogenic tumour spread and better general prognosis. Another example consists of stomach tumours. These can be divided into two main histological categories, the intestinal type and the diffuse type (Lauren, 1965). Tumours of the intestinal type but not of the diffuse type are often accompanied by chronic gastritis B and particularly by intestinal metaplasias, which are regarded as precursors of dysplastic changes and adenocarcinomas of the intestinal type (Jida et Kusama, 1982; Jass, 1983; Kato et al., 1981; Sipponen et al., 1983; Sirula et al., 1974; Strickland et Mackay, 1973). Pathogenetic differences between these two types of adenocarcinoma are also reflected in the observation that patients with tumours of the diffuse type often belong to blood group A, which indicates a possible influence of genetic factors on the risk of cancer (Piper, 1978), whereas environmental factors such as infections with *Helicobacter pylori* may be important in the development of tumours of the intestinal type (Parsonnet et al., 1991; Nomura et al., 1991). It would be desirable to be able to distinguish between tumours of the intestinal type and those of the diffuse type by means of molecular markers. Finally, cervical carcinoma of the uterus may be mentioned as a third example. In spite of a decreasing incidence (Petterson, 1988) the prognosis for patients with advanced stages of cervical carcinomas is poor (Perez et al., 1983; Park et Thigpen, 1993; Brady et al., 1986). Early diagnosis is based on the assessment of early morphological changes in the epithelial cells (cervical smear). Here again it is desirable to discover definite molecular markers for early cancer detection which can be used for staging and as prognostic factors.

It has recently been shown that the expression of variants of the surface glycoprotein CD44 is necessary and sufficient to trigger so-called spontaneous metastatic behaviour both in a non-metastasising pancreas adenocarcinoma cell line in rats and also in a non-metastasising fibrosarcoma cell line in rats (Gunthert et al., 1991). Whereas the smallest CD44-isoform, the standard form CD44s, is expressed ubiquitously in a series of different tissues, including epithelial cells, certain splice variants of CD44 (CD44v) are expressed only on a subgroup of epithelial cells. The CD44-isoforms are produced by alternative splicing so that the sequences of 10 exons (v1–v10) in CD44s are excised completely, but in the larger variants they may occur in different combinations (Screaton et al., 1992; Heider et al., 1993; Hofmann et al., 1991). The variants differ in that different amino acid sequences are inserted at a specific point in the extracellular part of the protein. These variants can be detected in different human tumour cells and in human tumour tissue. Thus, the expression of CD44-variants in the course of colorectal carcinogenesis has recently been investigated (Heider et al., 1993). There is no expression of CD44-variants in normal human colon epithelium and only slight expression can be detected in the proliferating cells of the crypts. At later stages of the tumour progression, e.g. in adenocarcinomas, all malignant degenerations express variants of CD44. Furthermore, the expression of CD44-splice variants has recently been demonstrated in activated lymphocytes and in non-Hodgkin's lymphomas (Koopman et al., 1993).

The objective of the present invention was to develop new methods of diagnosing and analysing tumours and providing agents for such processes.

This objective has been achieved with the present invention. It relates to a process for diagnosing and/or analysing tumours, particularly carcinomas, which is characterised in that variant CD44 is used as a molecular marker.

The preferred processes are those which are based on detecting the expression of individual, defined, variable exons of the CD44-gene or defined combinations of such exons. It may be beneficial to investigate the expression of different variant exons in a sample and compare them with one another.

Particularly preferred are the processes which are based on detecting the expression of the variable exons v5 and v6 and/or detecting the combined expression of exons v7 and v8.

The processes according to the invention may be carried out on samples outside the human or animal body or in vivo.

Advantageously, the processes according to the invention may be used to investigate samples from patients in whom there is already a suspicion of breast, stomach, colon or cervical cancer or in whom cancer has already been diagnosed but the tumour needs to be characterised more accurately. In particular, in the case of a suspicion or diagnosis of colon carcinoma expression of the variant exon v6 may be investigated, in cases of suspicion or diagnosis of breast or stomach cancer expression of the exon v5 and/or v6 may be investigated and when there is suspicion or diagnosis of cervical cancer the combined expression of the variable exons v7 and v8 may be investigated.

Variant CD44-molecules may be detected at the protein level using antibodies or at the nucleic acid level using specific nucleic acid probes or primers for the polymerase chain reaction (PCR). The invention therefore also relates to antibodies and nucleic acids which are suitable as probes or primers for such processes, and the use of these antibodies and nucleic acids for diagnosing and analysing tumours, particularly carcinomas.

Accordingly, the invention preferably also relates to antibodies against epitopes coded by exons v5, v6, v7 and/or v8, and nucleic acids which may hybridise with the exons v5, v6, v7 and/or v8, as well as primers which may be used for RT-PCR-amplification of RNA containing the exons v5, v6, v7 and/or v8. If the combined expression of the variant exons v7 and v8 is to be investigated, this is preferably done with an antibody directed against an epitope coded by these exons together (transitional epitope).

For in vivo diagnosis the CD44v-specific antibodies may be connected, for example, to a detectable marker e.g. a radioisotope, and injected into the vascular system of a patient. After selective binding of the antibodies to the tumour the latter can be visualised using a suitable detection system. Procedures for immunodiagnostic processes of this kind in vivo are known in the art (Thomas et al., 1989).

The nucleic and amino acid sequence of the variant exons of the CD44-gene is known (Hofmann et al., 1991, Screaton et al., 1992, Tolg et al., 1993). The existence of degenerate or allelic variants is of known significance to the performing of the invention; therefore, such variants are expressly included.

The sequence of exon v5 of the human CD44-gene and the corresponding amino acid sequence is (SEQ ID NO: 1 and (SEQ ID NO: 2):

```
    (D)   V   D   R   N   G   T   T   A   Y   E   G   N   W
(CAG)AT GTA GAC AGA AAT GGC ACC ACT GCT TAT GAA GGA AAC TGG

N   P   E   A   H   P   P   L   I   H   H   E   H   H   E
AAC CCA GAA GCA CAC CCT CCC CTC ATT CAC CAT CAG CAT CAT GAG

E   E   E   T   P   H   S   T   S   T
GAA GAA GAG ACC CCA CAT TCT ACA AGC ACA A.
```

The sequence of exon v6 of the human CD44-gene is (SEQ ID NO: 3) and (SEQ ID NO: 4):

```
     Q   A   T   P   S   S   T   T   E   E   T   A   T   Q
TC CAG GCA ACT CCT AGT AGT ACA ACG GAA GAA ACA GCT ACC CAG

K   E   Q   W   F   G   N   R   W   H   E   G   Y   R   Q
AAG GAA CAG TGG TTT GGC AAC AGA TGG CAT GAG GGA TAT CGC CAA

T   P   R   E   D   S   H   S   T   T   G   T   A
ACA CCC AGA GAA GAC TCC CAT TCG ACA ACA GGG ACA GCT G.
```

The sequence of exon v7 of the human CD44-gene and the corresponding amino acid sequence is (SEQ ID NO: 5) and (SEQ ID NO: 6):

```
     A   S   A   H   T   S   H   P   M   Q   G   R   T   T
CA GCC TCA GCT CAT ACC AGC CAT CCA ATG CAA GGA AGG ACA ACA

P   S   P   E   D   S   S   W   T   D   F   F   N   P
  CCA AGC CCA GAG GAC AGT TCC TGG ACT GAT TTC TTC AAC CCA

I   S   H   P   M   G   R   G   H   Q   A   G   R   R
  ATC TCA CAC CCC ATG GGA CGA GGT CAT CAA GCA GGA AGA AGG

M   D
  ATG G.
```

The sequence of exon v8 of the human CD44-gene and the corresponding amino acid sequence is (SEQ ID NO: 7) and (SEQ ID NO: 8):

```
     M   D   S   S   H   S   T   T   L   Q   P   T   A   N
AT ATG GAC TCC AGT CAT AGT ACA ACG CTT CAG CCT ACT GCA AAT

P   N   T   G   L   V   E   D   L   D   R   T   G   P
  CCA AAC ACA GGT TTG GTG GAA GAT TTG GAC AGG ACA GGA CCT

L   S   M   T   T   Q
  CTT TCA ATG ACA ACG C.
```

The antibodies according to the invention are therefore preferably directed against epitopes within the amino acid sequences shown or the allelic variants thereof. An antibody against the transitional epitope v7/v8 will preferentially recognise, in particular, an epitope inside the amino acid sequence (SEQ ID NO: 9)

ASAHTSHPMQGRTTPSPEDSSWTDFFN-PISHPMGRGHQAGRRMDMDSSHSTTLQPT ANP-NTGLVEDLDRTGPLSMTTQ or an allelic variant of this sequence.

Also particularly preferred is a v6-specific antibody which binds to an epitope within the amino acid sequence (SEQ ID NO: 10)

QWFGNRWHEGYRQT or an allelic variant of this sequence.

Particularly preferred are the monoclonal antibodies. However, other antibody molecules may be used for the process according to the invention, such as Fab- or F(ab')$_2$-fragments of immunoglobulins, recombinantly produced single-chain antibodies (scFv), chimeric or humanised antibodies and other molecules which bind specifically to epitopes coded by exons v5, v6, v7 and/or v8. The production of antibodies against known amino acid sequences may be carried out using methods known per se (Catty, 1989). For example, a peptide of this sequence may be produced synthetically and used as an antigen in an immunising programme. Another method is to produce a fusion protein containing the desired amino acid sequence by integrating a nucleic acid (which may be produced synthetically or by polymerase chain reaction (PCR) from a suitable probe) which codes for this sequence in an expression vector and expressing the fusion protein in a host organism. The optionally purified fusion protein can then be used as an antigen in an immunisation programme and insert-specific antibodies or, in the case of monoclonal antibodies, hybridomas which express insert-specific antibodies can be selected by suitable methods. Such methods are part of the prior art. Heider et al. (1993) and Koopman et al. (1993) describe the production of antibodies against variant epitopes of CD44.

It is also possible to perform the invention using nucleic acids which hybridise with variant exons, particularly v5, v6, v7 and/or v8, particularly those with more than 80% homology with the corresponding exon sequences. Such nucleic acids may be produced by methods known per se. This also applies analogously to primers which may be used in RT-PCR of RNA for detecting the expression of exons v5, v6, v7 and/or v8.

The process according to the invention for diagnosing and/or analysing tumours, particularly carcinomas, may appropriately be carried out by investigating samples taken from the body, such as biopsies. The agents according to the invention may advantageously be used.

For example, tissue sections may be investigated immunohistochemically with the antibodies according to the invention using methods known per se. Extracts or body fluids obtained from tissue samples may also be investigated using other immunological methods using the above-mentioned antibodies, for example in Western blots, enzyme-linked immunosorbent assays (ELISA, Catty and Raykundalia, 1989), radioimmunoassays (RIA, Catty and Murphy, 1989) or related immunoassays.

The expression of variant exons may be detected at the nucleic acid level, for example by hybridising RNA obtained from tissue samples (Northern blot) or RT-PCR-amplified RNA with suitable primers or by hybridising nucleic acids in tissue sections with suitable probes (in situ hybridisation).

The investigations may be carried out qualitatively, semi-quantitatively or quantitatively.

Data collected by detecting and/or quantifying the expression of variant CD44-epitopes may thus be included in diagnosis and prognosis. Advantageously it may be combined with other prognostic parameters, such as gradation.

The processes and agents according to the invention are exceptionally suitable for the diagnosis and/or analysis of tumours, particularly carcinomas. This is demonstrated by the Examples which follow. Thus, v5- and v6-expression are good prognostic parameters for breast cancer. Comparative investigation of v5- and v6-expression makes a substantial contribution to the differential diagnosis of intestinal and diffuse stomach cancer. In colon carcinoma v6-expression correlates very well with the stage of the tumour. The detection of expression of the transitional epitope coded by v7/v8 is a significant diagnostic parameter in the diagnosis of cervical carcinoma.

FIGURES

FIG. 1: Schematic representation of a CD44-molecule containing the variant exons v2 to v10. The shaded boxes indicate CD44-standard sequences (CD44s). TM=transmembrane domain. The rough location of the epitopes recognised by various monoclonal (black bar) and polyclonal (grey bar) antibodies is shown. The antibodies VFF7, VFF8 and VFF16 are each specific to an exon, whereas mAb VFF17 reacts with an epitope which is coded by exons v7 and v8 together.

Figure 2:
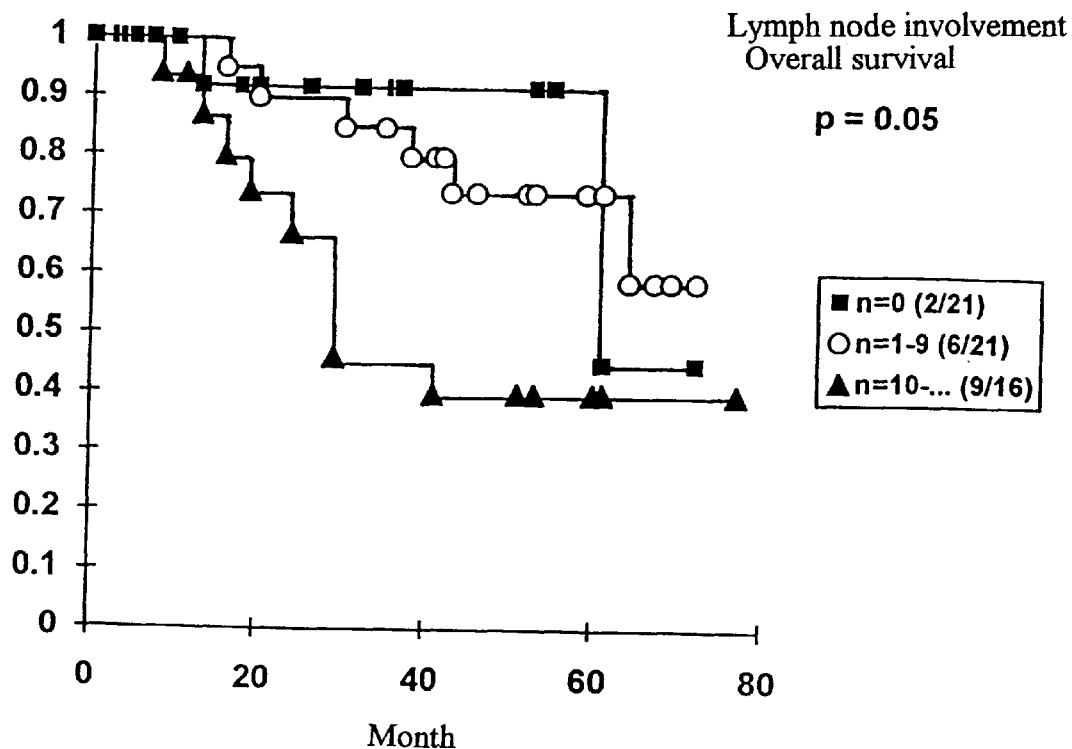

FIG. 2: Actuarial survival curve for breast cancer patients showing the correlation between lymph node involvement and survival time, calculated on the basis of the Kaplan-Meier calculation and logarithmic series test.

Figure 3:
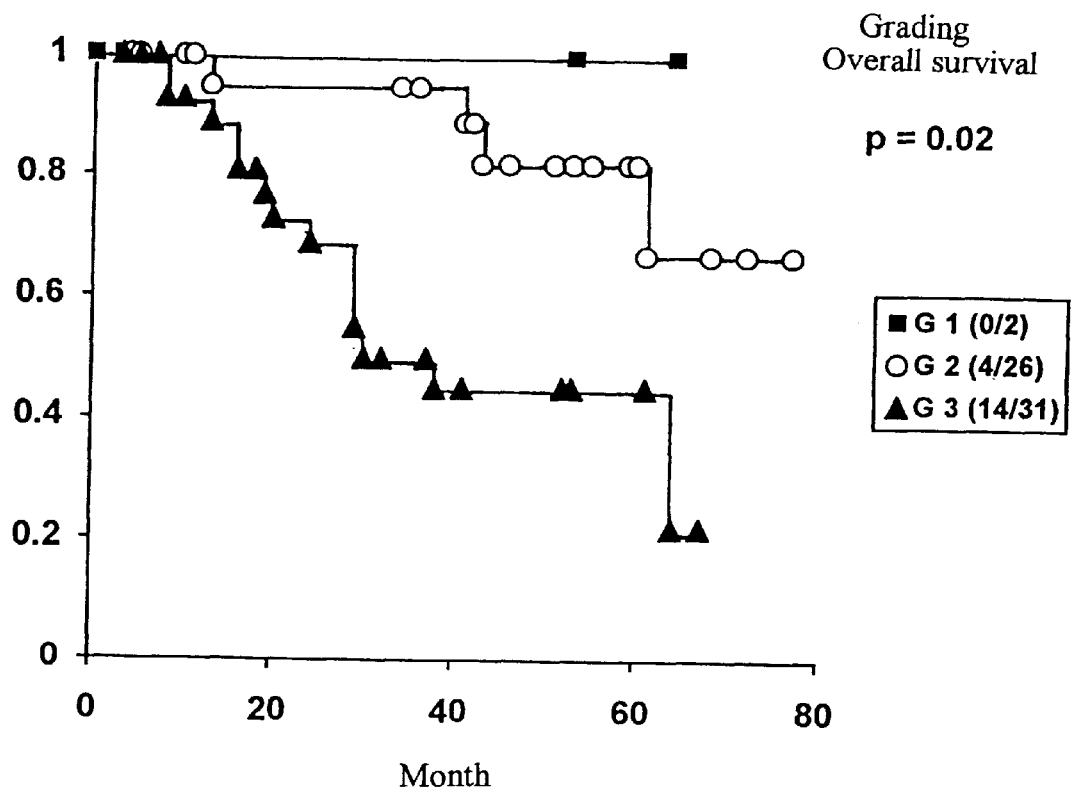

FIG. 3: Actuarial survival curve for breast cancer patients showing the correlation between tumour gradation and survival time, calculated on the basis of the Kaplan-Meier calculation and logarithmic series test.

Figure 4:
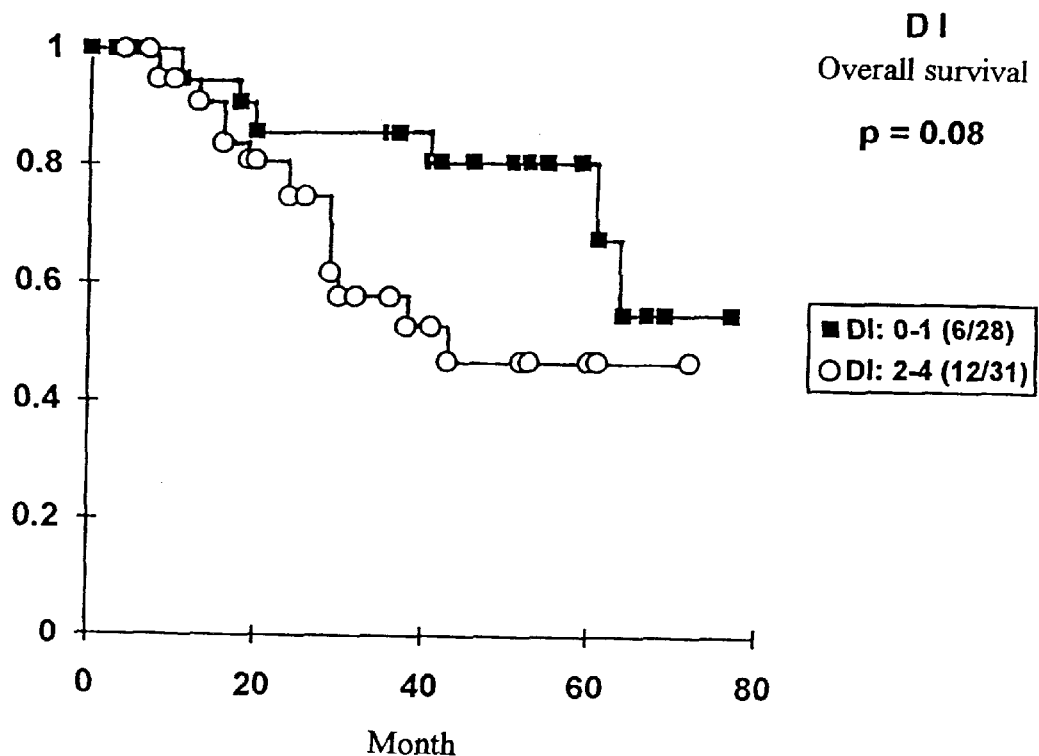

FIG. 4: Actuarial survival curve for breast cancer patients showing the correlation between exon-v3-expression and survival time, calculated on the basis of the Kaplan-Meier calculation and logarithmic series test. Patients with primary invasive breast cancer which expresses the CD44-v3-epitope versus non-expresser. 6/28 patients with v3-negative primary tumour and 12/31 with a v3-positive tumour died during the observation period of 70 months.

Figure 5:
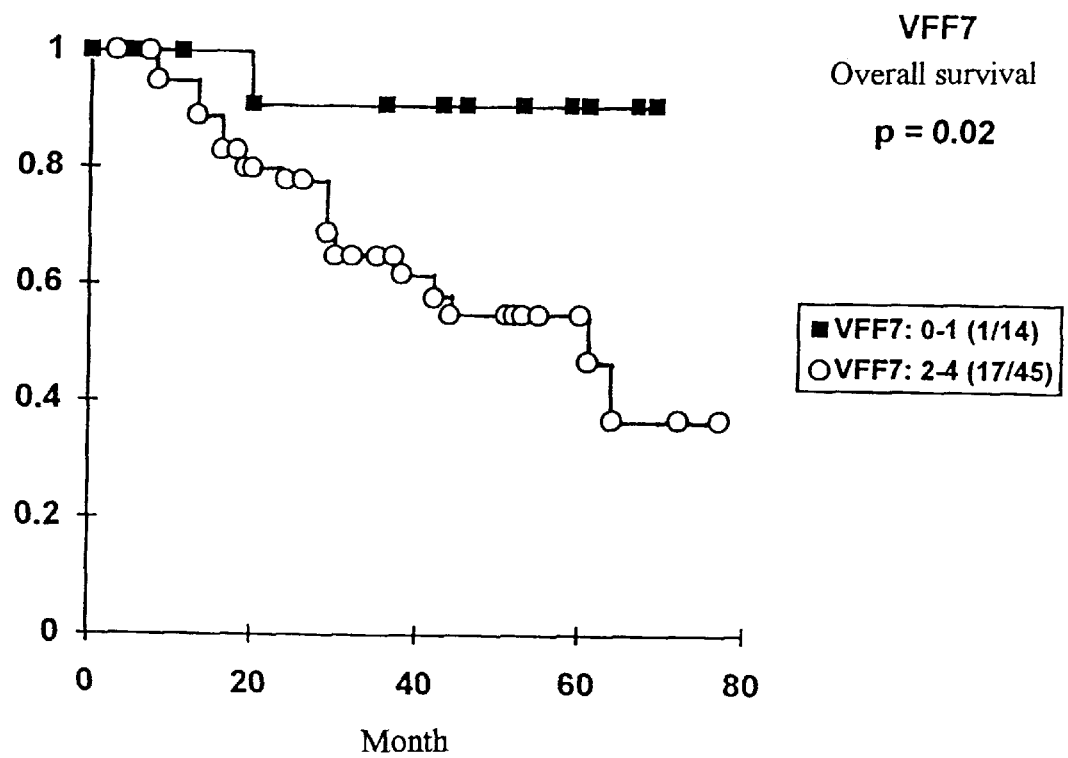

FIG. 5: Actuarial survival curve for breast cancer patients showing the correlation between exon-v6-expression and survival time, calculated on the basis of the Kaplan-Meier calculation and logarithmic series test. Patients with primary invasive breast cancer which expresses CD44-v6-epitope versus non-expressers. 1/14 patients with v6-negative primary tumour and 17/45 with v6-positive tumour died during the observation period of 70 months.

Figure 6:
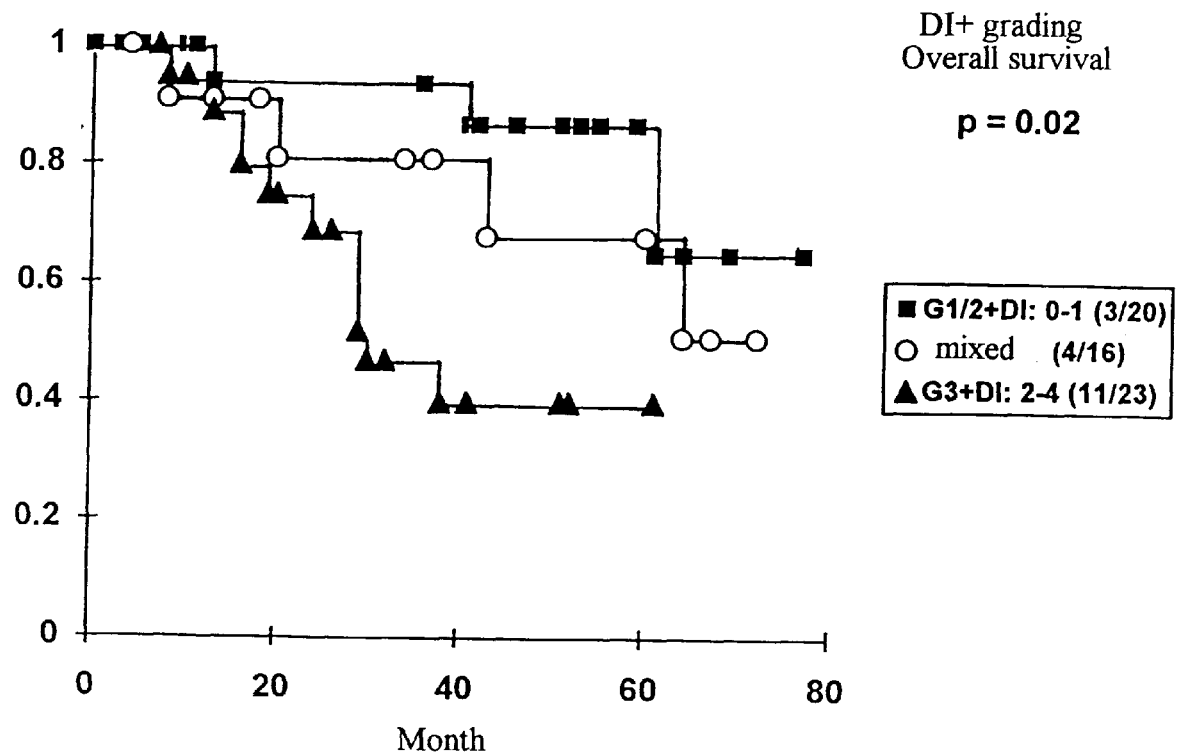

FIG. 6: Actuarial survival curve for breast cancer patients showing the correlation between v3-expression, combined with gradation, and survival time, calculated on the basis of the Kaplan-Meier calculation and logarithmic series test.

Figure 7:
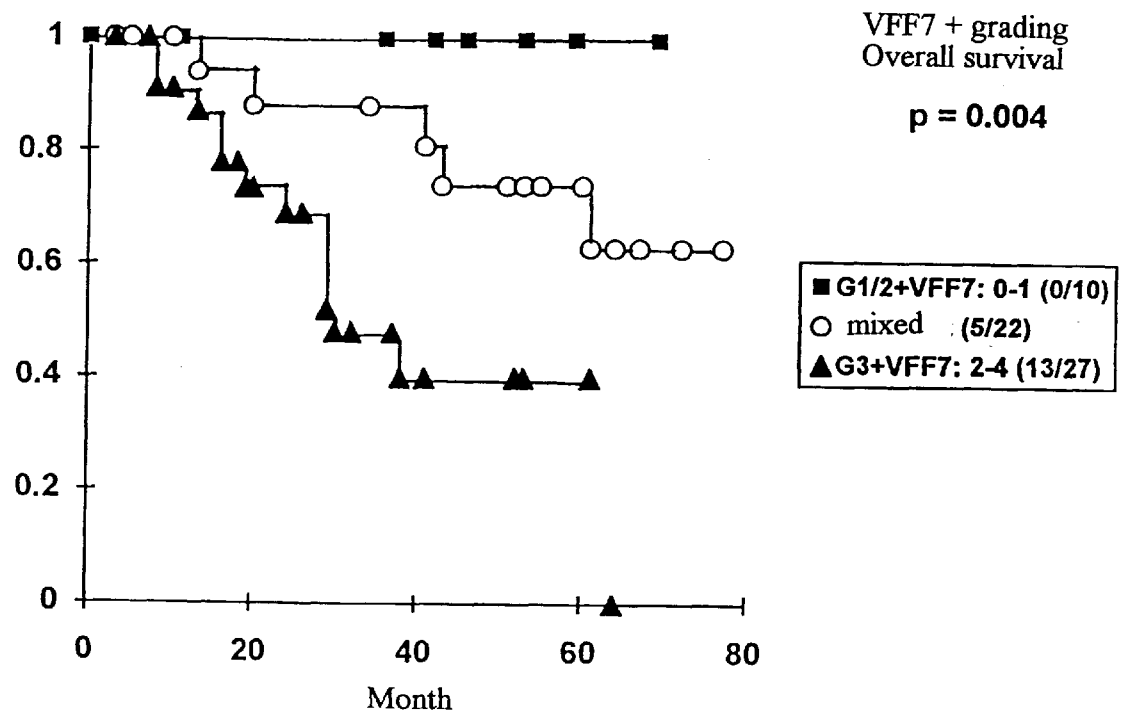

FIG. 7: Actuarial survival curve for breast cancer patients showing the correlation between v6-expression, combined with gradation, and survival time, calculated on the basis of the Kaplan-Meier calculation and logarithmic series test.

Figure 8:

FIG. 8: CD44v-expression in human breast cancer. Immunohistochemistry of a ductally invasive breast cancer with anti-CD44v-antiserum. (A): Primary tumour. (B): Lymph node metastases. Counterstaining: haematoxylin. Original magnification: 20×.

Figure 9:
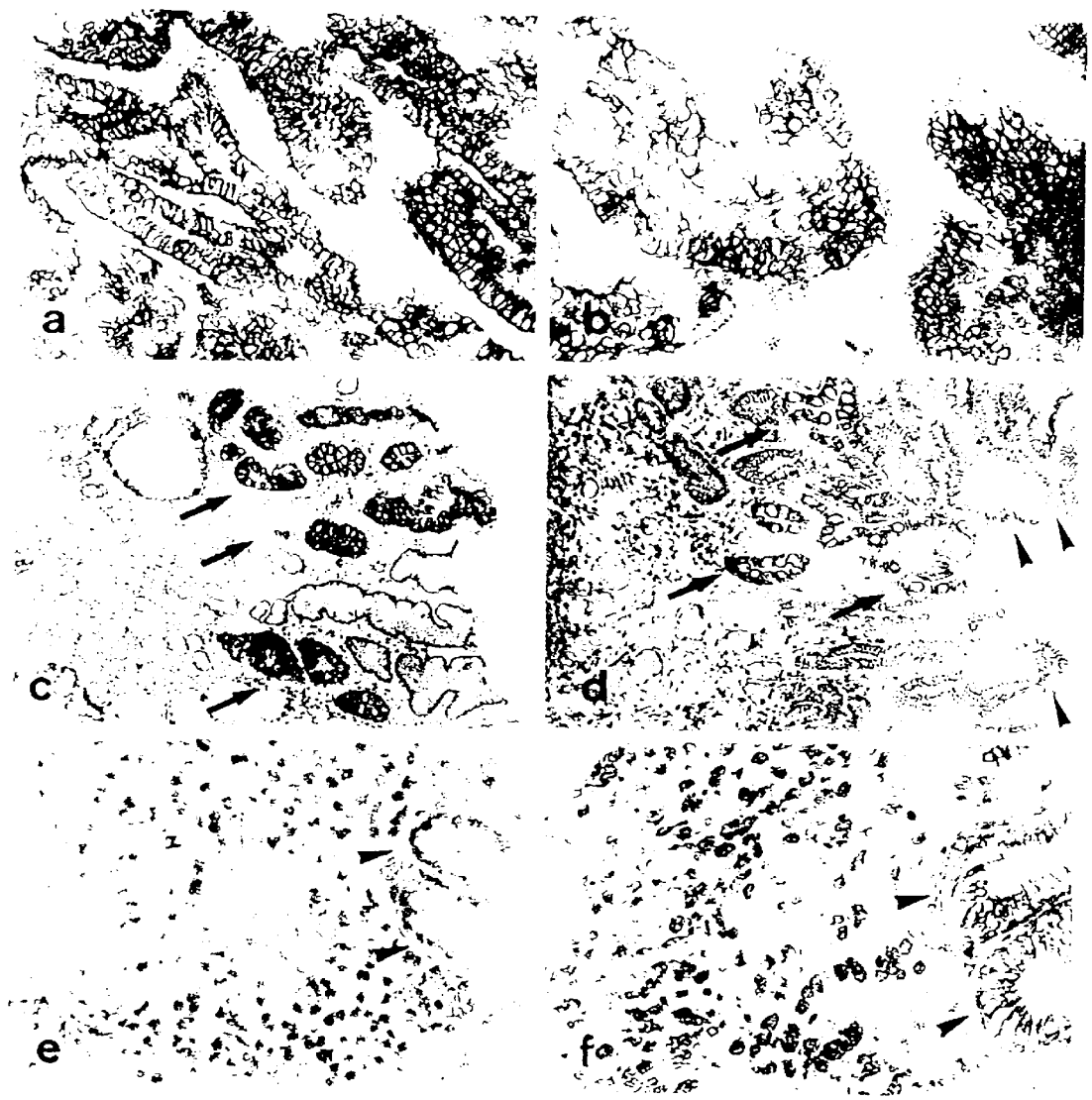

FIG. 9: Immunohistochemistry of normal mucosa and adenocarcinomas of the stomach. A focally emphasised anti-CD44v-positive reaction is found in tumour cells of a moderately differentiated adenocarcinoma (intestinal type according to Lauren) of the stomach (a) and in regional lymph node metastasis (b). In normal mucosa of a stomach with chronic gastritis the foci of intestinal metaplasias react positively with mAb VFF4 (c, arrows) and with mAb VFF8 (d, arrows), accompanied by an additional reaction on the mucoidal surface and the foveolar epithelium (d, tips of arrows). Almost all goblet cell carcinomas of the stomach (diffuse type according to Lauren) show a negative reaction with mAb VFF4 (e), and, unlike adenocarcinomas of the intestinal type, the normal mucoidal epithelium is negative (e, tips of arrows). In most cases, in these goblet cell carcinomas, there is a positive reaction with mAb VFF8 (f), and the remaining normal mucoidal epithelium also shows immunoreactivity (f, tips of arrows).

(ABC Method. (a), (b): anti-CD44v polyclonal serum, 140×; (c): VFF4, 80×; (d): VFF8, 80×; (e): VFF4, 210×; (f): VFF8, 210×; counterstaining haematoxylin).

Figure 10:
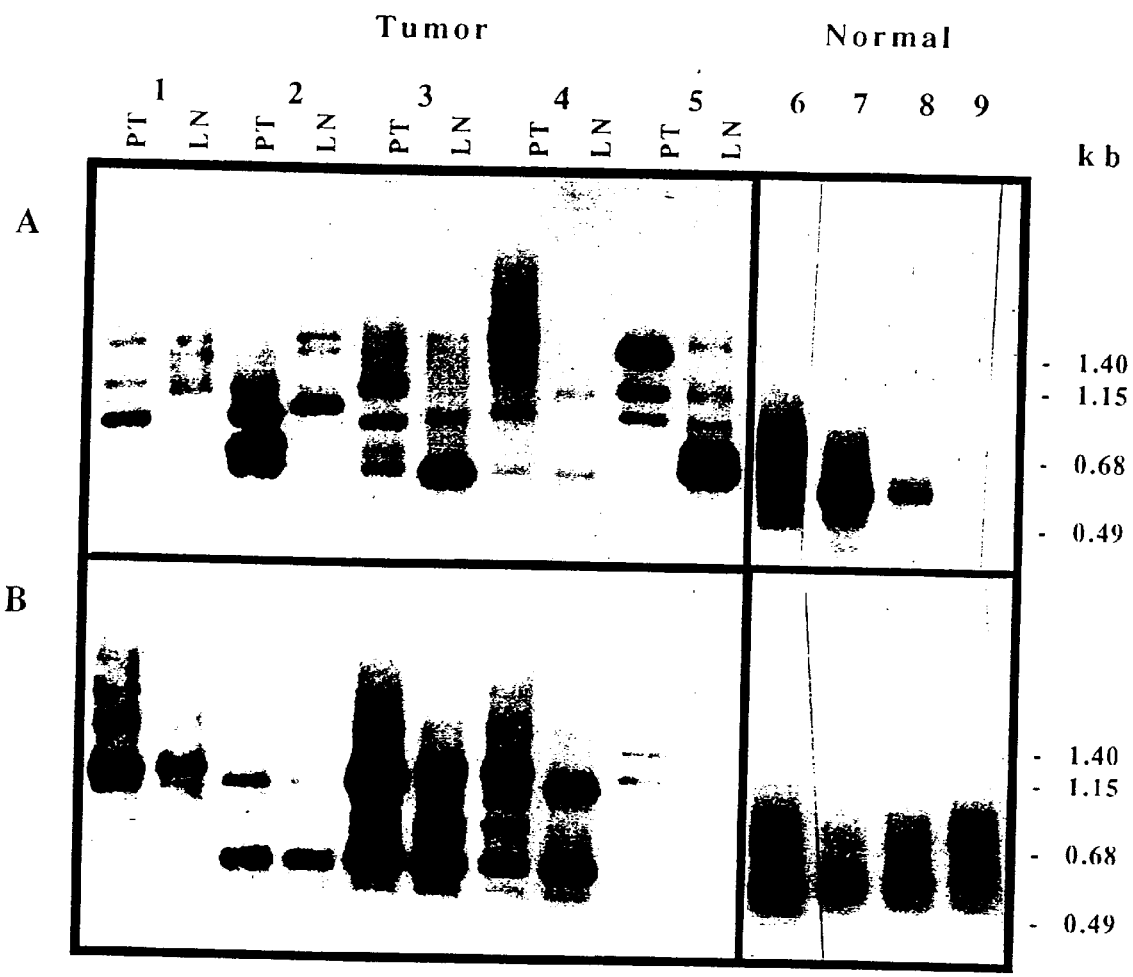

FIG. 10: Southern blot analysis of PCR-amplification products of individual samples from normal gastric mucosa, from primary stomach tumours and corresponding lymph node metastases. The PCR-primers were specific for CD44-exons adjacent to the variant exon sequences. cDNAs were produced by reverse transcription and, before the CD44-specific amplification, they were monitored by GAPDH-PCR in order to assess the quality and frequency of the synthesised cDNAs. The PCR-products obtained with the CD44-standard primers were separated by electrophoresis in a 1.2% agarose gel and transferred to Hybond $N^+$-membranes (Amersham, Braunschweig, Germany). The same filters were hybridised successively with exon-v6-specific (positions 243 to 356 of the published human CD44v-sequence according to Hofmann et al., 1991) (A) and exon-v6-specific (positions 360 to 482) (B) probes. Traces 1 to 5: 5 different primary adenocarcinomas of the stomach (PT) with corresponding lymph node metastases (LN) which were not contained in the collection of samples investigated immunohistochemically; traces 1 to 4: intestinal type; trace 5: diffuse type, traces 6 to 9: normal gastric mucosa from four different patients from the corpus region (traces 6–8) and antrum region (trace 9).

Figure 11:
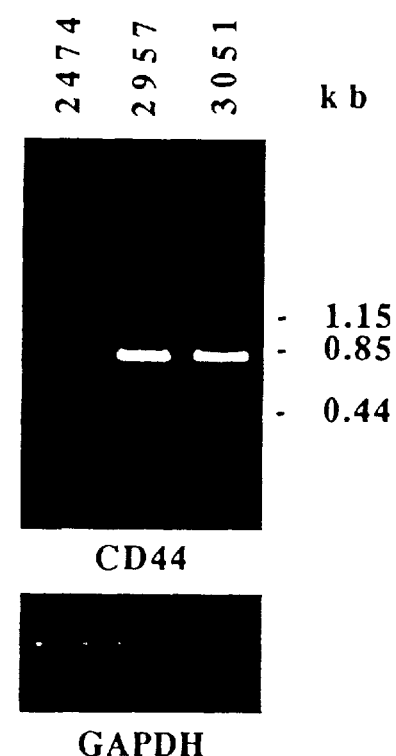

FIG. 11: Reverse transcription/PCR-amplification of CD44-transcripts in stomach cancer cell lines. Upper part: PCR-amplification products after the use of CD44-standard primers. The first strand synthesis was carried out using polyadenylated RNA from the gastric carcinoma cell lines 2474, 2957 and 3051. Lower part: GADPH-specific PCR-amplification products of the same RNA samples. The samples were separated in a 1.2% agarose gel, stained with ethidium bromide and made visible under UV-light.

Figure 12:
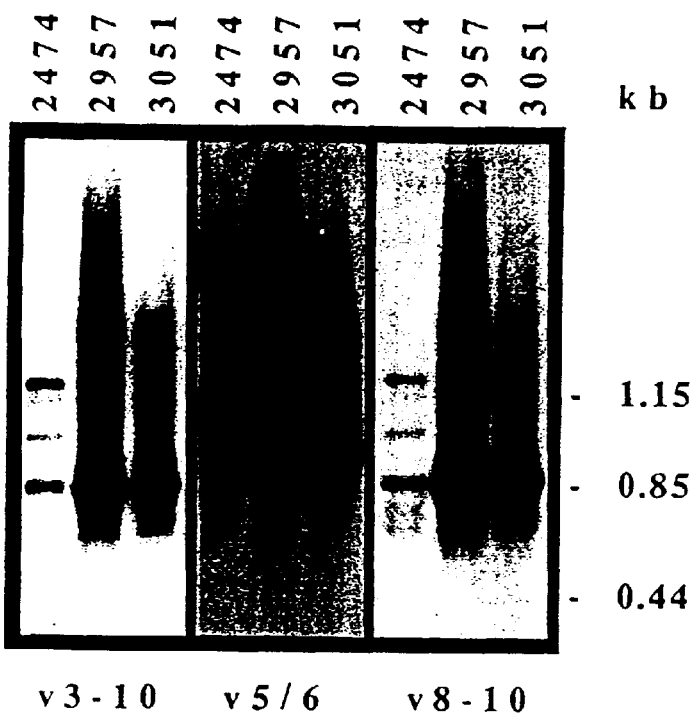
Figure 12:
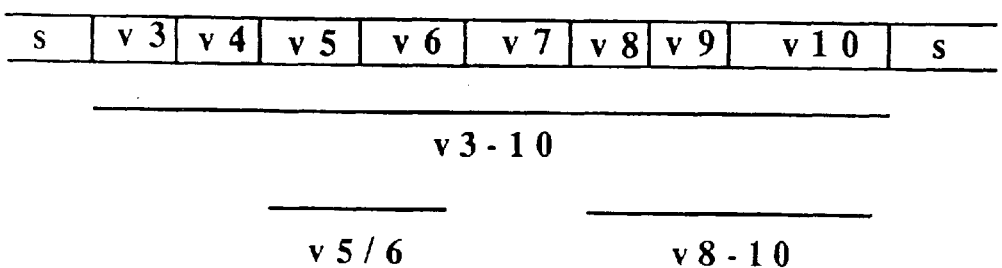

FIG. 12: Southern blot analysis of CD44-PCR-amplification products in gastric carcinoma cell lines. The PCR-reactions in FIG. 11 were separated in a 1.2% agarose gel, transferred to a Hybond N+-membrane and hybridised successively with samples specific to different variant CD44-exons. v3–10 contains nucleotides from position 25 to 1013; v5/v6 contains nucleotides from position 244 to 468; v8–10 contains nucleotides from position 623 to 981 of the published human variant CD44-exon sequences (Hofmann et al., 1991).

Figure 13:
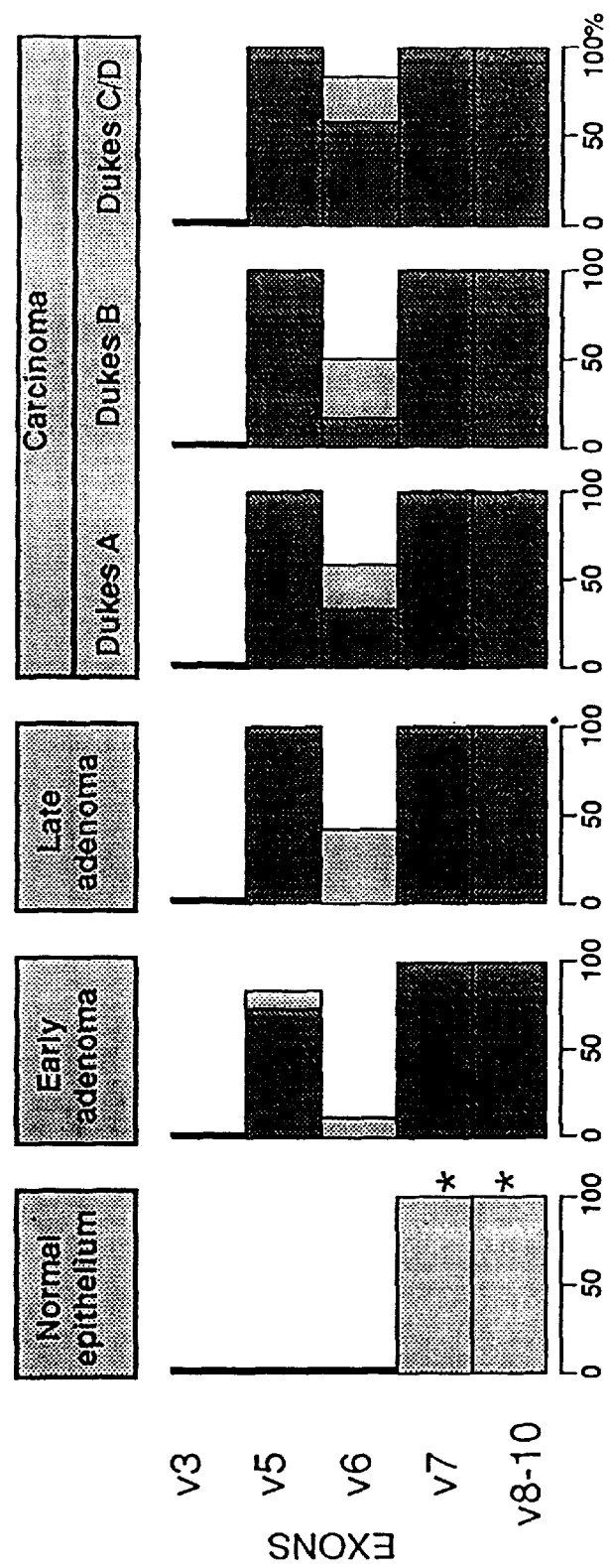

FIG. 13: Expression of variant CD44-exons at various stages of colorectal tumour progression. Results of immunohistochemical stainings of tissue sections.

Figure 14:
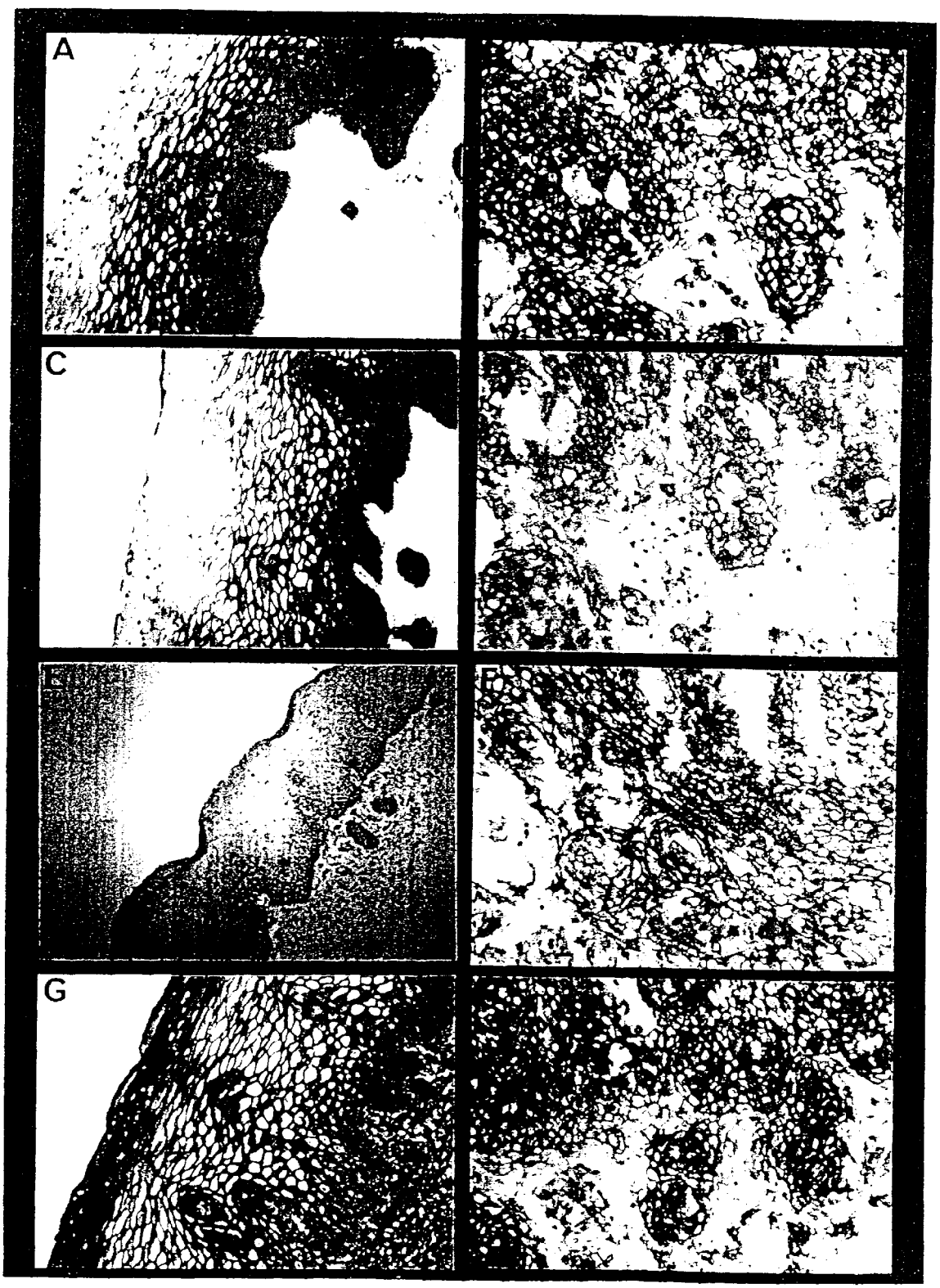

FIG. 14: Immunohistochemistry of normal cervix epithelium (A, C, E, G) and a plate epithelial carcinoma of the cervix. (B, D, F, H). All normal cervical tissue samples show a strong staining reaction with the polyclonal sera anti-CD44v3-v10 (A) anti-v3-v4 (C), anti-v6-v7, VFF7, VFF8 and VFF16 (not shown). The staining reactions were restricted to the stratum basale and the stratum spinosum, whilst the stratum superficiale remains unstained. The mAb VFF17 showed no staining at all of normal epithelial cells (E). The mAb SFF2 which is directed against CD44s stained all cell layers deeply (G). Most of the cervical carcinoma samples showed strong staining reactions with all polyclonal sera and mAbs including mAb VFF17. Representative examples are shown in Figures (B) (anti-CD44v3-v10), (D) (mAb VFF7), (F) (VFF17), and (H) (mAb SFF2). Avidin-biotin-peroxidase-complex method. Magnification: ×140 (A-D, F-H, ×80 (E); counterstaining: haematoxylin.

Figure 15:
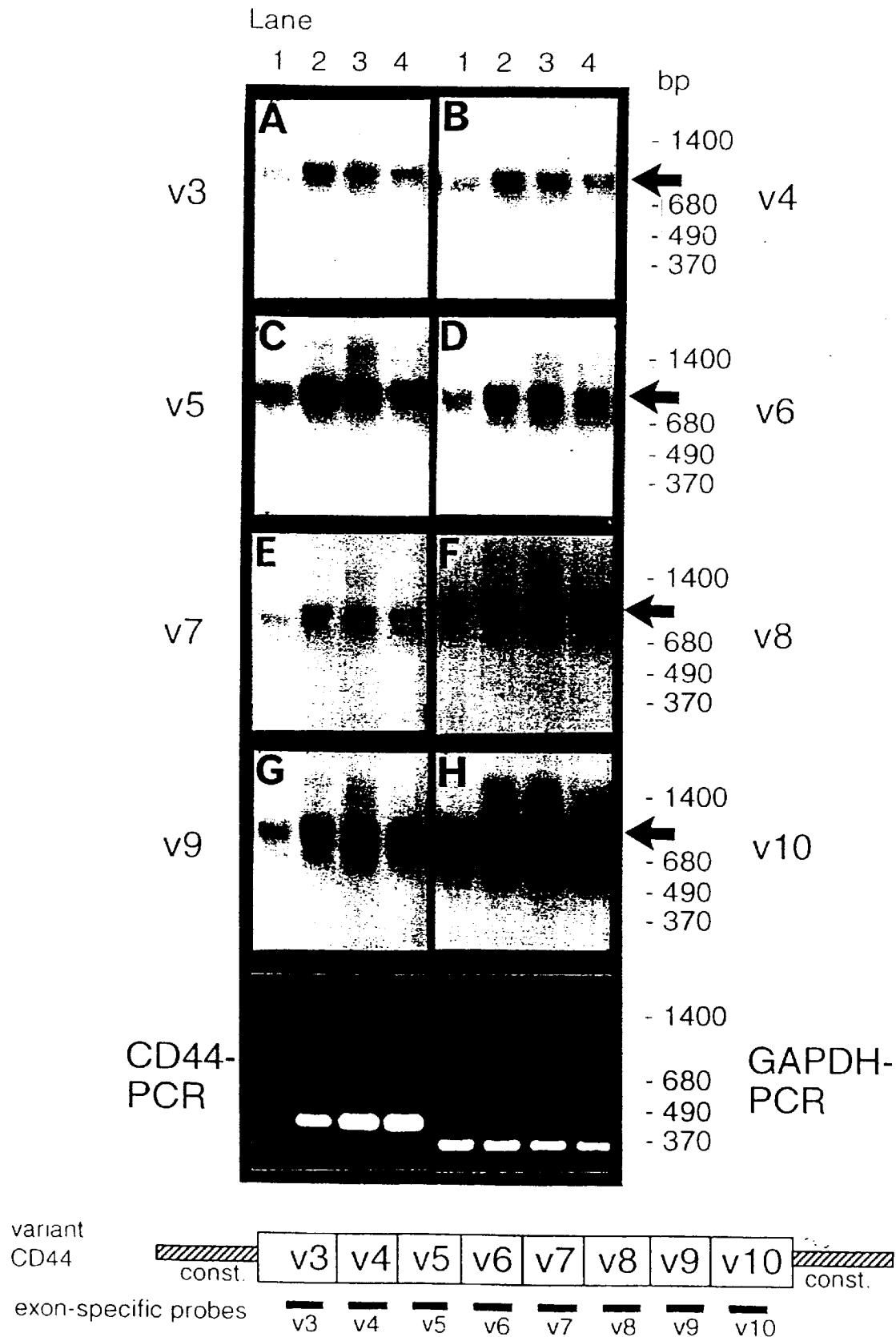

FIG. 15: Southern blot analysis of PCR-amplification products of individual samples of normal tissues of the Cervix uteri. The PCR-primers were specific for CD44-exons in the vicinity of the variant exon sequences. cDNAs were produced by reverse transcription and tested, before the CD44s amplification with glycerinaldehyde-phosphate-dehydrogenase-PCR in order to test the quality and quantity of the synthesised cDNAs (K). The PCR-products obtained with CD44-standard-primers were separated on 1.2% agarose (I) and transferred to a Hybond-N+-membrane (Amersham). The same filter was then hybridised successively with probes which were specific for the variant exons v3–v10 (A–H) as shown in the Figure. Traces 1–4: normal cervix samples from 4 different patients. Exposure time: 45–60 minutes.

Figure 16:
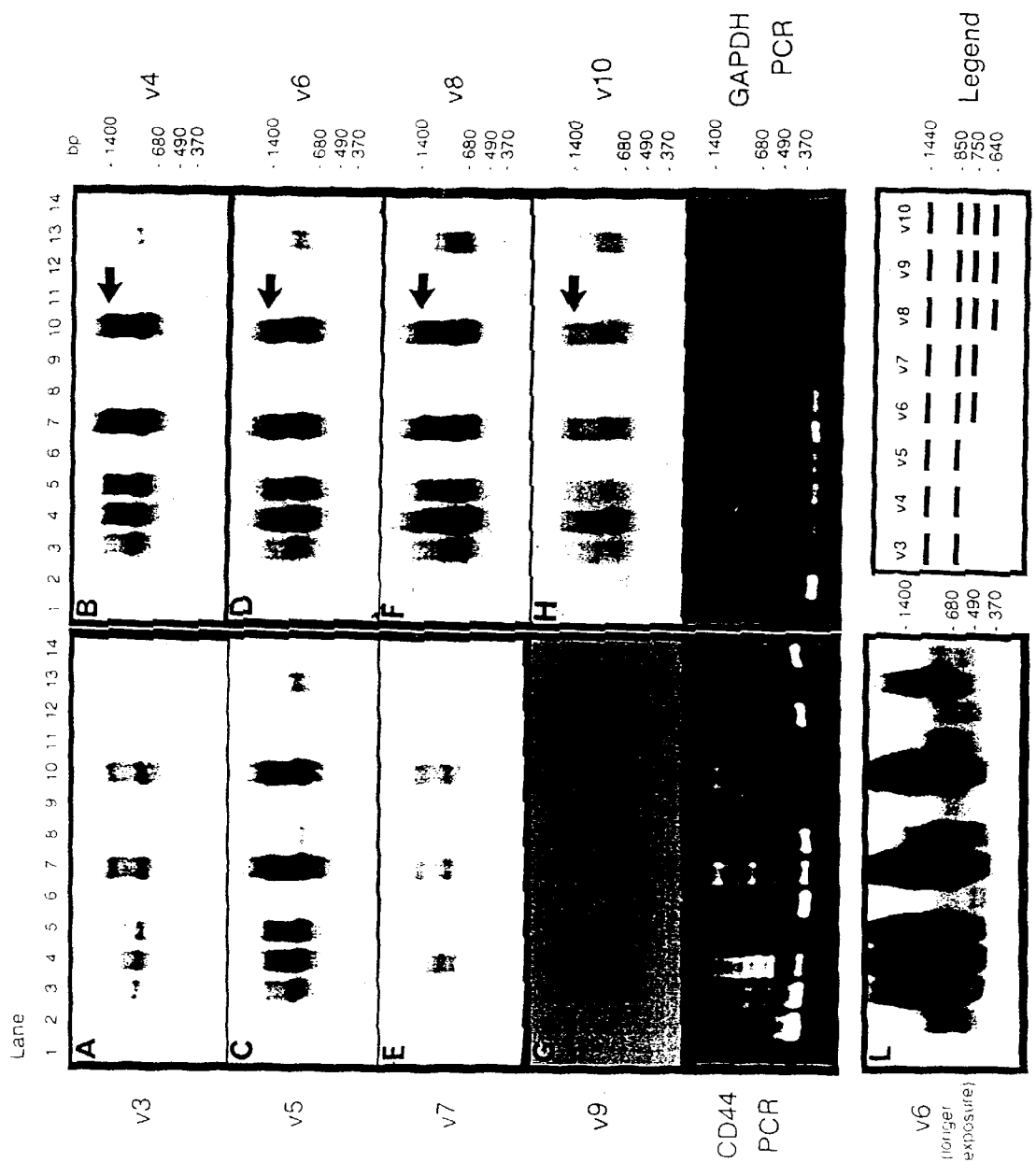

FIG. 16: Southern blot analysis of PCR-amplification products from individual samples of tumours of the Cervix uteri. The PCR-primers were the same as described in FIG. 15. The PCR-products obtained with CD44-standard primers were separated on an agarose gel (I). After Southern blotting the filter was hybridised successively with samples which were specific for the variant exons v3–v10 (A–H) as shown in the Figure. Trace 1: negative control; trace 2: sample of breast tumour as positive control; traces 3–14: samples of cervical tumours from 12 different patients. Trace 7 shows the same tumour as in FIG. 14. Exposure time: 2–5 minutes (A–H), 15–20 minutes (L).

The suitability of the process according to the invention for diagnosing and/or analysing tumours will be demonstrated hereinafter by way of example in the case of breast, stomach, colon and cervical cancers.

EXAMPLES

Example 1

Diagnosis and analysis of breast cancers 1.1. Tumours and tissue

Frozen tissue (stored at −70° C.) was obtained from the University Womens Clinic in Heidelberg, Germany. It was used for immunohistology, using the antibodies described below. 61 samples of primary breast cancers, 9 local recurrences of breast cancers, 4 cases of pure in situ carcinomas and 16 axillary lymph node metastases (from the same patients as the primary tumours) were included. The cases were selected at random and included a representative selection of histological tumour types, stages and gradations. For comparison, samples of normal breast tissue, ductal hyperplasias and fibroadenomas were used.

1.2. Production of antibodies against epitopes coded by variant exon sequences of the CD44-gene 1.2.1. Cloning of pGEX-fusion proteins The entire variant region of the HPKII-type of CD44v (Hofmann et al., 1991) was amplified from human keratinocyte-cDNA by polymerase chain reaction (PCR). The two PCR-primers 5'-CAGGCTGGGAGCCAAATGAAGAAAATG-3' (SEQ ID NO: 11), positions 25–52, and 5'-TGATAAGGAACGATTGACATTAGAGTTGGA-3' (SEQ ID NO: 12), positions 1013–984 of the LCLC97-variant region, as described by Hofmann et al., contained an EcoRI-recognition site, which was used to clone the PCR-product directly into the vector pGEX-2T (Smith et al., 1988). The resulting construct (PGEX CD44v HPKII, v3–v10) codes for a fusion protein of ~70 kD, consisting of glutathione-S-transferase from *Schistosoma japonicum* and the exons v3–v10 of human CD44 (FIG. 1; Heider et al., 1993). The fusion protein was expressed in *E. coli* and then purified by affinity chromatography over glutathione-agarose (Smith et al., 1988).

In order to obtain subclones of the variant regions which could be used for affinity purifications and Western blot analyses, fragments were cloned containing DI (v3), DII/III (v5, v6), and DIII (v6, v7), using the appropriate restriction cutting sites. Fusion protein DI contains the CD44-sequence described by Stamenkovic et al. (1989), from position 744 to position 142 of the sequence of variant CD44 as described by Hofmann et al. (1991). Fusion protein DII/III contains the variant sequence of position 290–460, fusion protein DIII the variant sequence of position 378–638 (Hofmann et al., 1991). The fragments containing DI and DIII were cloned into the pGEX-vector system and the DII/III fragment into the pATH-vector (Angel et al., 1988).

1.2.2. Monoclonal antibodies: immunisation and screening

Female Balb/c mice were immunised intraperitoneally with affinity-purified fusion protein (GST-CD44v3–10). In the 1st immunisation, 90 μg of fusion protein were administered in complete Freund's adjuvant and in the 2nd and 3rd immunisations 50 μg of fusion protein was administered each time in incomplete Freund's adjuvant. The immunisations were carried out at an interval of 4 weeks. 14 days after the last immunisation the animals were immunised on three successive days with 10 μg of fusion protein in PBS. The following day, spleen cells from an animal with a high antibody titre were fused with P3.X63-Ag8.653 mouse myeloma cells using polyethyleneglycol 4000. The hybridoma cells were then selected in microtitre plates in HAT-medium (Köhler and Milstein, 1975; Kearney et al., 1979).

The measurement of the antibody titre in the serum and the screening of the hybridoma supernatants were carried out using an ELISA. In this test, first of all microtitre plates are coated with fusion protein (GST-CD44v3–10) or only with glutathione-S-transferase. Then they were incubated with serial dilutions of serum samples or hybridoma supernatants and the specific antibodies were detected with peroxidase-conjugated antibodies against mouse immunoglobulin. Hybridomas which reacted only with glutathione-S-transferase were discarded. The remaining antibodies were first characterised in an ELISA with domain-specific fusion proteins (exon v3, exon v5+v6, exon v6+v7, exon v8–v10) (Koopman et al., 1993). Their immunohistochemical reactivity was tested on sections of human skin.

The exon specificity of various antibodies is shown in FIG. 1. VFF7 recognises an epitope in the amino acid sequence of exon v6. VFF8 recognises an epitope in the amino acid sequence of exon v5. VFF-17 recognises an epitope coded by exons v7 and v8 together. The antibodies NKI-PI and SFF2 recognise epitopes in the standard part of the extracellular domains near the N-terminus 1.2.3 Polyclonal antibodies The production and purification of polyclonal antisera against the variant region of the CD44-molecule are described in the literature (Heider et al., 1993). The exon specificity of the total serum (anti-CD44v) and affinity-purified fractions (anti-DI, anti-DIII) is shown in FIG. 1.

1.3. Immunohistochemistry of tissue sections of breast cancers and evaluation by comparison with other prognostic factors Immune stainings were carried out according to standard procedures as described hereinbefore (Heider et al., 1993). Frozen sections (6–7 μm) were fixed in ice cold methanol for 4 min., then in acetone for 1 min., washed in PBS (8 g/l NaCl, 0.2 g/l KCl, 1.44 g/l $Na_2HPO_4$, 0.24 g/l $KH_2PO_4$, pH 7.4) and preincubated with normal goat serum (10% in PBS). They were then washed 3× with PBS and incubated for 1 hour with the primary antibody (in PBS, 1% BSA). A final concentration of 5 μg/ml was used for monoclonal antibodies. Affinity-purified polyclonal sera were titrated on normal skin keratinocytes in order to obtain optimum staining results. Endogenous peroxidase was blocked with 0.3% $H_2O_2$ in methanol and the sections were incubated with biotinylated second antibodies (either anti-mouse or anti-rabbit $F(ab')_2$, DAKO Corp., Santa Barbara, Calif., USA, depending on the primary antibody used). The immune complex was visualised with horse-radish peroxidase which was coupled to biotin as streptavidin-biotinperoxidase complex (DAKO). After thirty minutes incubation with the streptavidin-biotin-peroxidase complex the sections were developed with 3,3-amino-9-ethyl-carbazole (Sigma Chemicals, Deisenhofen, Germany) for 5 to 10 minutes and the reaction was stopped with $H_2O$. The cells were counterstained with haematoxylin, covered with glycerol-gelatine and examined under the microscope.

The expression of splice variants was evaluated in a total of 60 primary breast tumours. In 59 patients, follow up tests were carried out over a sufficiently long period of time (on average 35 months, range 3–77), to allow evaluation of the prognostic influence. The average age of the patients was 51 (31–79). 21 women had no axillary lymph node metastases. Between one and nine positive nodes were found in 21 patients, 10 or more occurred in 16 patients. 11 patients were given no further adjuvant therapy after the primary surgical therapy, whilst 12 patients were treated with 30 mg of tamoxifen for 2 years and 36 patients were each given six cycles of cytotoxic chemotherapy. The frozen sections were coded and evaluated in various laboratories independently of one another for nuclear and histological grading and for immunohistological staining with antibodies against the v6-epitope. Evaluation of the stained slides was carried out without any knowledge of the course of the disease. Other CD44-epitopes were examined in parallel. The staining was evaluated on a scale from 0–4. Staining of 0–1 was regarded as negative (14 patients), and staining of 2–4 was regarded as positive (45 patients).

The tumour samples investigated were almost 100% positive for one of the CD44-isoforms, whereas normal breast epithelium and benign hypertrophies did not express CD44. 82% of these tumours carried the v6-epitope. A typical staining pattern for a tumour section is shown in FIG. 8. All the lymph node metastases (16 cases) were v6-positive, indicating that v6-expression is correlated to an advanced tumour stage.

The semiquantitative evaluation of the immunological reactions surprisingly showed a close correlation between v6-expression and prognosis. The expression of other epitopes investigated, e.g. v3 or v10, did not yield such a close correlation. The univariate survival analysis (Table 1) showed that high expression of the variant epitope v6 (antibody VFF7) is a significant prognostic parameter for a poor overall survival time (OAS, p=0.02, Table 1 and FIG. 5). The prognostic value is better than that of the lymph node status (p=0.05) and that of the S-phase fraction (p=0.03) and comparable with that of histological grading. In addition, the connection between lymph node involvement or v6-expression and OAS was investigated using a multivariate Cox-regression analysis (Table 2). The risk ratio was smaller in patients with a small number of lymph node metastases compared with those having numerous positive nodes. The expression of the v6-epitope also correlated with an increased risk ratio. Evaluation of the v6-epitope is superior to the lymph node status as a predictor of OAS. The same is true of v5-expression. Univariate survival analysis showed that high expression of the epitope v5 (antibody VFF8) is also a significant prognostic parameter for a poor overall survival time (p=0.02). The v3-epitope also shows a connection with a poor OAS, but only at the limits of significance (p=0.08, Table 1 and FIG. 4). By contrast, v10-expression is a significantly worse prognostic parameter (p=0.3). The differences between the expression rates of the variant exons can be explained by the existence of mixed populations in which different splice variants exist side by side. Although the presence of v3- and v6-sequences is correlated (p=0.001), v6 is the better determinant of tumour progression. High v6-expression correlates significantly with positive lymph node status (p=0.05) and high S-phase content (p=0.008) and histological grading (p=0.06). The combination of v6-surface expression and histological grading improves the prognostic significance. All patients whose primary tumours had a low v6-content and were well differentiated survived the disease (FIG. 7). More than 50% of the patients who had v6-positive primary tumour cells of grade 3 died within 65 months. If one of the two factors was unfavourable, the survival rate was intermediate (p=0.004). The combination of v3-epitope and histological grading was no better than grading on its own (p=0.02). Adjuvant cytotoxic therapy was more effective when the tumour did not express v6 (p=0.07) than when it did.

The investigation clearly demonstrates the surprising prognostic value of the process according to the invention, particularly based on the expression of the variant exons v5 and v6, for breast cancer.

TABLE 1

Univariate analysis for comparing overall survival time (OAS) in relation to conventional prognostic factors and the expression of the splice variants v3 and v6 in 59 breast cancer patients using Petos logarithmic series test

| Parameter | | OAS p-value |
|---|---|---|
| Age of patient at diagnosis | (<50/≧50 years) | 0.5 |
| Size of primary tumour | (<2/<5/≧5 cm) | 0.6 |

TABLE 1-continued

Univariate analysis for comparing overall
survival time (OAS) in relation to conventional
prognostic factors and the expression of the splice
variants v3 and v6 in 59 breast cancer patients using
Petos logarithmic series test

| Parameter | | OAS p-value |
|---|---|---|
| Grading | (I/II/III) | 0.02 |
| Axillary lymph nodes involved | (0–3/≧4) | 0.05 |
| Lymph vessels involved adjacent to the tumour | (negative/positive) | 0.03 |
| Tumour | | |
| Oestrogen receptor | (<20/≧20 fmol/mg) | 0.001 |
| Progesterone receptor | (<20/≧20 fmol/mg) | 0.001 |
| Ploidity, DNA index | (<1.1/≧1.1) | 0.8 |
| Percentage of cells in the S-phase fraction | (<5/≧5%) | 0.1 |
| Exon v3 (DI) | (Evaluation 0–1/2–4) | 0.08 |
| Exon v5 (VFF8) | (Evaluation 0–1/2–4) | 0.02 |
| Exon v6 (VFF7) | (Evaluation 0–1/2–4) | 0.02 |
| Exon v10 (VFF16) | (Evaluation 0–1/2–4) | 0.3 |
| Exon v3 + grading | (0/1/2 unfavourable parameters) | 0.02 |
| Exon v6 + grading | (0/1/2 unfavourable parameters) | 0.004 |

TABLE 2

Multivariate analysis showing the results
of a proportional risk regression analysis of the
simultaneous influence of the nodal status and the
surface expression of the CD44-v6-epitope on the OAS.
Cox's partial non-parametric regression model was used
to determine the predictive power of the combinations of factors.

| Factor | Calculated risk ratio | p-value |
|---|---|---|
| Lymph node status 0–3 as against ≧4 | 2.45 | 0.12 |
| v6, negative versus positive | 5.56 | 0.10 |

Example 2
Diagnosis and analysis of gastric carcinomas
2.1. Tumours and tissue

Tumour samples and normal tissue were selected from the supplies kept by the Pathology Department of the University of Würzburg in Germany. The samples were flash-frozen immediately after surgical removal and stored at −80° C. until ready for use. Normal tissue was taken from twelve different tumour patients and from the corpus and antrum region of the stomach. Pathological tissues were obtained from a total of 47 patients with an average age of 63. Of the primary carcinomas 29 were of the intestinal type and 18 of the diffuse type according to Lauren (1965). The tumour stages ranged from localised (pT1) to extensive (pT4) and the histological grading from well differentiated (G1) to poorly differentiated (G3) adenocarcinomas.

2.2. Immunohistochemistry of gastric tumours

The production of the antibodies used and the procedure for immune stainings were as described in Example 1.

Polyclonal antisera directed against the epitopes v3–v10 (CD44v in FIG. 1) stained 42 out of 42 frozen sections of stomach tumours (Table 3, Examples in FIGS. 9a, b). The staining was heterogeneous in terms of its intensity and distribution. Between 5% and 100% of the tumour cells were stained with different intensities. This confirms the findings of Heider et al. (1993) that adenocarcinomas express CD44-splice variants. However, the tests which follow surprisingly showed that fine analysis of the expression pattern of the different variant exons is suitable for diagnosing and/or analysing gastric carcinomas. Both qualitative and semi-quantative conclusions may be drawn.

Frozen sections of tumours were investigated with exon-specific monoclonal antibodies (mAbs). Almost all the tumours which reacted positively with the polyclonal antiserum also reacted positively with an mAb against an exon-v5-specific epitope (VFF8; Table 3; an example is shown in FIG. 9f). By contrast, the reaction with the v6-specific antibody VFF4 was much more restricted, only 26 out of 42 tumours reacted positively (Table 3). Mabs which recognised other exons (v3/4, v7, v8–10), did not bind (Table 3).

Surprisingly, 23 of the 26 VFF4-positive tumours were adenocarcinomas of the intestinal type, whereas 14 of the 16 v6-negative cases were signet-ring carcinomas of the diffuse type (an example is shown in FIG. 9c). The present invention thus provides for the first time a molecular marker for distinguishing different subtypes of gastric carcinomas.

Both primary tumours and lymph node metastases could be obtained from 10 patients. Five of these pairs belonged to the intestinal type and five to the diffuse type. Epitopes recognised by the polyclonal antiserum were present both on the primary tumours and on the metastases of all 10 pairs of tumours (Table 4; FIGS. 9a and 9b show the primary tumour No. 9069/90 in Table 4 and the associated lymph node metastasis). All the tumour samples (primary tumours and metastases) reacted with the mAb VFF8 which is specific for exon v5. All the samples belonging to the intestinal type reacted positively after incubation with the mAb VFF4 which is specific for exon v6, whilst of the signet ring carcinomas only one pair belonged to the VFF4$^+$-group (see Table 4). No differences were discovered in the intensity of colour between primary tumours and metastases, nor were there any consistent differences in the proportion of CD44v-positive cells between the primary tumour and metastases (Table 4). This applies particularly to the lymph metastases of the VFF4 (exon v6)-negative signet ring carcinomas of the diffuse type, which also did not react with this mAb (Table 4). The present invention thus provides for the first time a process and means for carrying it out by which direct conclusions can be drawn regarding the primary tumour of an adenocarcinoma by analysis of metastases using molecular markers.

In order to investigate whether the expression of CD44v in adenocarcinomas, particularly of the stomach, is a result of the transformation process, or whether CD44 is already expressed in normal tissue, e.g. of the gastrum, frozen sections of normal gastric mucosa from twelve different patients were analysed by immunohistochemical staining with antibodies specific for CD44-variants. All twelve samples stained positive with the polyclonal serum and with some of the monoclonal antibodies. With the polyclonal antiserum (exons v3–v10) and the mAb VFF8 (exon sequence v5) positive reactions were obtained on the mucoid surface epithelium, in the foveola proliferation zone and in areas of intestinal metaplasia (an example is shown in FIG. 9d). Interestingly, these latter areas also reacted positively with VFF4 (exon sequence v6), whilst other parts of the normal gastric epithelium did not react with this mAb (FIG. 9c). All other mAbs (VFF11, VFF9, VFF14; epitope specificity, cf. FIG. 1) failed to react. In certain areas of the gastric mucosa a splice variant of CD44 is thus expressed which carries the exon sequence v5 and therefore resembles the cells of carcinomas of the diffuse type in its expression. Areas of the gastric mucosa characterised by intestinal metaplasia, on the other hand, carry epitopes of both exons v5 and v6 and are therefore similar to carcinomas of the intestinal type in their expression. These findings support the theory that the tumours originate from these types of cells and maintain the expression pattern of the cells from which they originate. The present invention for the first time makes it possible to analyse adenocarcinomas, particularly of the stomach, in this way.

TABLE 3

Expression of variant CD44-epitopes on the cell surfaces of gastric tumours

| Adenocarcinoma | Serum[1] αCD44v (v3–v10) | Monoclonal antibodies | | | | |
|---|---|---|---|---|---|---|
| | | VFF11 (v3/4) | VFF8 (v5) | VFF4 (v6) | VFF9 (v7) | VFF14 (v8–10) |
| Diffuse type | 17/17[2] | 0/17 | 14/17 | 3/17 | 0/17 | 0/17 |
| Intestinal type | 25/25 | 0/25 | 25/25 | 23/25 | 0/25 | 0/25 |
| All | 42/42 | 0/42 | 39/42 | 26/42 | 0/42 | 0/42 |

[1]polyclonal antiserum
[2]number of positive tumours/number of tumours investigated

TABLE 4

Expression of variant CD44-epitopes in primary tumours of the stomach and the corresponding lymph node metastases

| | Antibody specificity | | | | | |
|---|---|---|---|---|---|---|
| | polyclonal serum | | monoclonal antibodies | | | |
| | antiCD44v | | VFF8(v5) | | VFF4(v6) | |
| Adenocarcinoma[3] | Intensity | pos. cells PT/LN | Intensity | pos. cells PT/LN | Intensity | pos. cells PT/LN |
| Diffuse type | | | | | | |
| 645/89 | ++[4] | 100[5]/100[6] | ++ | 20/90 | − | 0/0 |
| 12589/89 | ++ | 40/50 | ++ | 80/90 | − | 0/0 |
| 12924/89 | ++ | 70/80 | ++ | 40/30 | − | 0/0 |
| 25501/89 | ++ | 90/70 | ++ | 70/70 | ++ | 30/30 |
| 33383/89 | ++ | 80/30 | ++ | 40/20 | − | 0/0 |
| Intestinal type | | | | | | |
| 32761/88 | ++ | 60/10 | + | 10/20 | + | 20/90 |
| 33295/88 | ++ | 90/10 | ++ | 80/60 | + | 40/40 |
| 9891/89 | +++ | 100/80 | ++ | 70/70 | ++ | 20/5 |
| 18352/89 | +++ | 90/90 | +++ | 90/80 | ++ | 70/50 |
| 9069/90 | ++ | 90/90 | ++ | 60/60 | + | 20/80 |

PT = primary tumour; LN = lymph node metastases
[3]The numbers refer to tumours and the corresponding lymph node metastases (not shown separately). The tumours are contained in the collection shown in Table 1.
[4]Intensity (because there was no difference in intensity between primary tumour and lymph node metastasis the common staining is shown here: − negative, + slight, ++ moderate, +++ intense
[5]Percentage of positive tumour cells in the primary tumour
[6]percentage of positive tumour cells in a lymph node metastasis in the same patient 2.3. Western blot analysis Cells were lysed by ultrasound and boiled for 3 minutes in SDS-gel sample buffer (Lämmli, 1970). Equal amounts of protein (detected by staining the gel with Coomassie Brilliant Blue) were separated by electrophoresis in a denaturing 6% polyacrylamide gel (Lämmli, 1970). The proteins were transferred onto polyvinylidene difluoride membrane (Millipore, Eschborn, Germany), using a Transblot device (BIO-RAD Laboratories, Munich, Germany). Non-specific interactions were blocked by pre-incubating the membranes with a powdered milk suspension (10% dried milk powder in PBS). The membranes were then incubated at ambient temperature with the polyclonal anti-CD44-antiserum (see FIG. 1), followed by further incubation with goat anti-rabbit IgG conjugated with alkaline phosphatase (Amersham, Braunschweig, Germany). The incubation period was one hour in each case. After each antibody incubation the membranes were washed with PBS containing 0.3% Tween 20 (Sigma). The binding of the antibodies was detected using an Enhanced Chemoluminescent System (Amersham).

2.4. Reverse Transcription/PCR-amplification

In order to investigate whether the expression patterns of the splice variants in normal tissue and in tumour tissue are the same or different, RNA was isolated from normal tissue and from tumours, reversetranscribed, amplified by PCR and hybridised with exonspecific samples. For the PCR, primers located at the 5'- or 3'-side of the insertion site of the variant exons were used.

2 μg of total RNA (from tissues) or polyA$^+$-RNA (from cell lines) were isolated and reverse-transcribed as described in the literature (Günthert et al., 1991). 5 μl of the first strand cDNA were amplified with Taq-polymerase (Amersham) in 50 μl under the buffer conditions recommended by the manufacturer. For the GAPDH-PCR, oligonucleotides were used which were homologous to positions 8–29 and 362–339 of the published cDNA sequence (Allen et al., 1987). After 26 amplification cycles (95° C. for 1 minute, 62° C. for 1 minute, 72° C. for 2.5 minutes) 10 μl of the reaction medium were separated in a 1.4% agarose gel and the amplification product was stained with ethidium bromide and visualised under UV-light. For amplification of the variant CD44-transcripts, primers were used which were homologous to positions 513–540 (5'-oligo) and 900–922 (3'-oligo) of the published human CD44-sequence (Stamenkovic et al., 1989). After 36 amplification cycles (94° C. for 1 min., 62° C. for 1 min., 72° C. for 2.5 min.) 10 μl of the reaction medium were separated in an agarose gel, the gel was stained with ethidium bromide and visualised under UV-light and then transferred onto nylon membranes in order to carry out the Southern blots (cf. FIGS. 10 and 12 and the associated captions) using standard procedures (Sambrook et al., 1985).

By ethidium bromide staining of agarose gels, a dominant PCR product corresponding in size to the CD44s was detected both in samples from normal mucosa and also in tumour samples. PCR products of less prominence were detected after transfer to nylon membranes and hybridisation with exon-specific probes (FIG. 10). By hybridisation with a v5-specific or a v6-specific probe the expression of RNA containing exon v5 or v6 was detected. There was a significant difference in the pattern of the RNA expressed in normal tissue and in tumours. The RNA patterns also differed from one tumour to another.

RNA from 10 of the 12 samples of normal stomach mucosa which had also been investigated by immunohistochemistry yielded two dominant bands which hybridised with exons v6 and two dominant bands of similar size which hybridised with exon v5 (four representative examples are shown in FIGS. 10A and B). RNA from tumour samples yielded a more complex and variable pattern of splice products. The tumours contained, at least partially, larger splice variants up to a size which leads one to presume the presence of all variant exon sequences (FIG. 10). Obviously, not all the epitopes coded by these exons were accessible for immunohistochemistry. Both tumours of the diffuse type and those of the intestinal type exhibited strong expression of transcripts which contained exon v5 (FIG. 10A, traces 1–5). Certainly there was a clear difference between tumours of the diffuse and intestinal types, with regard to hybridisation with the exon v6-specific probe. Whereas in all four samples of the intestinal type amplification products could be detected containing exon v6 (see FIG. 10B, traces 1–4), the sample of a tumour of the diffuse type showed almost no hybridisation with the v6-specific sample (FIG. 10B, trace 5). The present invention thus makes it possible to diagnose and analyse adenocarcinomas using molecular markers at the nucleic acid level, and provides the means to do so. In particular, the process according to the invention makes it possible to distinguish gastric carcinomas of the diffuse and intestinal type and to analyse the corresponding metastases at the nucleic acid level.

Example 3

Diagnosis and analysis of colon carcinomas 3.1. Tumours and tissue

Normal and pathological tissue was obtained from the supplies held by the Pathology Department, Academic Medical Centre, University of Amsterdam, Netherlands. Colorectal carcinomas (n=39) were divided into stages using Dukes classification (1937, 1980), in Dukes A (n=9), disease was restricted to the intestinal wall; Dukes B (n=14), spread beyond the layer of muscle without metastasis; Dukes C/D (n=16), tumours with regional or distant metastases. Adenomas were subdivided into early adenomas (diameter <1 cm, n=11) and late adenomas (diameter >1 cm, n=12) and were graded using standard criteria as being poorly or highly differentiated.

3.2. Immunohistochemistry of colon carcinomas

The production of the antibodies used and the immunostaining procedures are as described in Example 1.

A total of 70 normal and pathological colon samples were investigated. Tumours were termed "positive" if more than 10% of the tumour cells were stained. If fewer than 10% of the tumour cells were stained this was regarded as "focal".

The immunohistochemical examination of tissue samples yielded differential expression of variant CD44-proteins in normal colorectal mucosa, adenomatous polyps and colorectal carcinomas (FIG. 13). In the normal colon epithelium the expression of CD44-proteins is limited. Only slight coloration at the crypt base was found in the staining with a monoclonal antibody (mAb NKI-P1) against the N-terminal constant portion of CD44. A similar expression pattern was observed for the epitopes coded by the exons v8–v10.

Expression of other variant exons (v3–v6) could not be detected in normal colon epithelium (FIG. 13). Like the normal colon epithelium, colorectal tumours also express splice variants which contain the exons v8–v10. However, expression is much more intense and is no longer restricted to the crypts. Moreover, additional variants which are not present in normal colon epithelium are found in tumours. This overexpression and increasing variety of CD44-variants is observed even at very early stages of colorectal tumour progression, e.g. in early adenomas which, in addition to the exons v8–v10, largely express CD44-isoforms which contain v5 (FIG. 13). At more advanced stages of the colorectal tumour progression, e.g. in advanced polyps and invasive cancers, the degree of expression of v5-containing CD44-variants increases. However, it was surprising that the tumour progression correlated sharply with the expression of v6-containing CD44-isoforms (FIG. 13): expression of this exon was detectable in none of the normal colon samples, in 9% of the early polyps, in 45% of the advanced polyps and in 67% of the invasive cancers. (Chi-square 1 df p <0.0001). In addition, the expression of v6 in cancers correlated significantly with the Dukes stage. Whereas the proportion of positive samples in the non-metastatic Dukes A and B tumours was 52%, it was 83% in the metastatic Dukes C/D group (Chi-square 1 df p <0.05). Additionally, it was observed that the overexpression of v6 containing CD44-isoforms during the tumour progression is reflected not only by the increasing number of positive cases but also by an increasing number of positive cells within a tumour and by a higher level of expression (more intense staining of the cells). The focal expression of v6 in adenomas correlated with a further parameter of tumour progression, the histological tumour grade, the v6-expression being positive in none of 17 adenomas with a low grade but being positive in 5 out of 6 adenomas with a high grade.

Information as to the v6-expression, which may be obtained for example by routine immunohistochemistry, can therefore provide valuable information for diagnosis and prognosis of colon carcinomas owing to the surprising correlation, in particular, between the v6-expression and the tumour stage.

Example 4

Diagnosis and analysis of cervical cancers 4.1. Tumour and normal tissue samples Tumour and normal tissue samples of the neck of the womb were provided by the Gynaecology Department of Heidelberg University (Germany). All the samples were flash-frozen in liquid nitrogen immediately after surgical removal and stored at −80° C. until ready for use. 5 normal samples were obtained from patients who had undergone total hysterectomy in connection with nonneoplastic diseases. 16 cervical cancer samples (15 plate epithelial carcinomas and 1 adenocarcinoma) were also investigated. The stages of the tumours ranged from the FIGO stage Ib (n=7) through stage IIb (n=5) up to stage IIIb (n=4).

4.2. Immunohistochemistry of cervical carcinomas

The production of the antibodies used and the procedure used for immune stainings are as described in Example 1.

16 cervical carcinomas and 5 samples of normal cervix epithelium were examined for surface expression of N-terminal and variant epitopes of CD44 (FIG. 1) and for CD44-mRNA by using RT-PCR. These data allow one to draw conclusions both regarding (a) normal differentiation of the cervical epithelium and also (b) carcinogenesis.

(a) Epithelial differentiation. N-terminal epitopes are present on the subepithelial stroma cells and in all epithelial layers (FIG. 14G). The presence of N-terminal epitopes indicates CD44-promoter activity in all stroma cells and epithelial layers. Epitopes of variant exons do not occur in stroma cells but are strongly expressed in epithelial cells. These epitopes are lost in the direction of the epithelial surface and are absent from the stratum superficiale (FIGS. 14A, C). An epitope which is formed by the transitional fragment of exon v7 and v8 and is recognised by the mAb VFF17 (anti-v7/v8) is totally absent in the normal epithelium (FIG. 14E). The pattern of immune staining can be interpreted as showing the surface expression of one or more CD44-isoforms with regulated accessibility of the epitopes (e.g. by glycosylation) or with regulated synthesis by alternative splicing. The combination of exons v7/v8 indicated by the occurrence of the transitional epitope is ruled out. The O-glycosylation site near the 5'-end of exon v8 (G ünthert et al., 1991; Screaton et al., 1992) could be responsible for the inaccessibility of the epitope for the antibody. Regulated synthesis of CD44-isoforms which contain variant exons has been described in activated lymphocytes and skin keratinocytes (Arch et al., 1992). In the cervical epithelium the highly active and strongly proliferating basal cells show the highest CD44v-expression, whilst the calmer surface cells do not do this, although there is promoter activity, as shown by the evidence of the N-terminal epitope. Consequently, these differences represent changes in splicing or in glycosylation.

(b) Carcinogenesis. In clear contrast to the normal epithelium, 15 out of 16 samples of cervical tumours show the v7/v8 transitional epitope (FIG. 14F). This indicates that either there is a dramatic change in the modification of the epitopes or, which is more likely, there is a dramatic change in the splicing pattern. Although the immune staining is only semiquantitative, antibody dilution experiments also show that CD44-expression is more intense in all cancer cells compared with normal epithelium.

Information as to the combined expression of exons v7 and v8, as may be obtained, for example, by detecting the transitional epitope using routine immunohistochemistry, may also provide valuable findings for diagnosis and prognosis of cervical cancers, thanks to the surprising occurrence of this combined expression in tumour tissue but not in normal tissue.

4.3. Reverse transcription/PCR-amplification

To find out whether alternative splicing can be detected, RNAs were analysed by semiquantitative RT-PCR.

3 μg of total RNA (isolated from tumour or normal tissue) were isolated and reverse-transcribed as described earlier (G ünthert et al., 1991). 5 μl of the first strand cDNA were amplified with Taq-polymerase (Amersham) in a volume of 50 μl in Taq-polymerase buffer (Amersham). For the glycerinaldehyde-phosphatedehydrogenase PCR, oligonucleotides were used which were homologous to positions 8–29 and 362–339 4of the published cDNA sequence (Allen et al., 1987). In order to amplify the variant CD44-transcripts, primers were used which were homologous to positions 513–540 and 934–958 of the published human CD44-sequence (Stamenkovic et al., 1991). After 25 (GAPDH) or 30 (CD44) amplification cycles (1 minute at 94° C., 1 minute at 62° C., 2.5 minutes at 72° C.), 10 μl of the reaction mixture were separated in a 1.2% agarose gel. The amplification products were made visible after ethidium bromide staining and the CD44-products were then transferred on to nylon membranes (Hybond-N+, Amersham) for Southern blotting. $^{32}$P-labelled hybridisation probes were synthesised with PCR, using CD44v-exon-specific primers which were homologous to positions 24–53/81–110 (v3), 128–154/213–239 (v4), 243–271/327–356 (v5), 357–383/456–482 (v6), 489–515/585–614 (v7), 621–647/692–718 (v8), 722–750/779–808 (v9) and 812–838/987–1013 (v10) (Hofmann et al., 1991).

Hybridisation with probes for variant exons with long exposure provide evidence of the presence of alternatively spliced, long CD44-transcripts in the RNAsamples (FIG. 15). The largest fragment which occurs in all the samples, 850 minus 440 base pairs, could carry 3–4 variant exon sequences. This RNA species might possibly code CD44 v3–v6 or v4–v7. In addition, at least one other species is present, the so-called epithelial variant CD44v8–v10 (also with a transcript length of 850 bp). These data support the assumption that a CD44-isoform containing v7 and v8 at the same time does not exist, and provide evidence of the absence of the transitional epitope (v7/v8). The source of the CD44s-RNA cannot be clearly defined.

PCR data show that almost all samples of malignant tissue contain RNA for CD44-splice variants (FIG. 16). Traces 6 and 9 in FIG. 4 represent samples with only a small number of tumour cells. Therefore, the quantity of CD44v-RNA to be expected was too small to be amplified sufficiently. Certainly, the tumour cells exhibited intense expression of variant epitopes in the immune staining. Ethidium bromide staining provides evidence of the relative frequency of PCR-products in tumour samples compared with samples of normal epithelium (difference in intensity of hybridisation signals is 20-fold) (FIG. 15). It should be noted that the band representing CD44s could originate from RNA from tumour cells or stroma cells. The relative frequency of variant exon sequences differed from one sample to another. Interestingly, among the samples with the most intense expression and the largest number of different isoforms were those of patients who already had lymph node metastases at the time of the operation.

A large mRNA species (1440 minus 440 base pairs of the variant domain) which might correspond to an isoform of CD44 with exons v3–v10 was frequently produced in the cervical cancers investigated in this study. This could be the isoform which contains the v7/v8-transitional epitope. In addition, various smaller isoforms could be detected, whilst the hybridisation pattern could represent both CD44v3–v7, CD44v8–v10 and also other variants. It can be concluded that cervical cancers exhibit a two-fold change in CD44 expression: an increase in the production of CD44-splice variants and a change in the splice pattern, which leads to the acquisition of a new (transitional) epitope. Although it is not yet clear what molecular functions the various splice variants perform, the change in the splicing pattern appears to confer a selective advantage.

Bibliography

Allen, R. W., Trach, K. A., and Hoch, J. A. Identification of the 37 kDa protein displaying a variable interaction with the erythroid cell membrane as glyceraldehyde-3-phosphate dehydrogenase. *J. Biol. Chem.* 262: 649–652 (1987).

Angel P., Allegretto, E. A., Okuio, S. T. Hattan, K., Boyle, W. J., Hunter, T., Karin, M. Oncogen jun encodes a sequence-specific trans-activator similar to AP-1. *Nature* 332: 166 (1988).

Arch, R., Wirth, K., Hofmann, M., Ponta, H., Matzku, S., Herrlich, P., and Zöller, M. Participation in normal immune responses of a splice variant of CD44 that encodes a metastasis-inducing domain. *Science* 257: 682–685 (1992).

Brady, L. W., Perez, C. A., Bedwinnek, J. M. Failure patterns in gynecologic cancer. *Int. J. Rad. Oncol. Biol. Phys.* 12: 549–557 (1986).

Catty, D (Hrsg). *Antibodies Vols. I and II.* IRL Press Oxford (1989).

Catty, D., Raykundalia, C. ELISA and related immunoassays. In: Catty, D (Hrsg). *Antibodies Vol. II.* IRL Press Oxford (1989), 97–152, p. 105–109.

Catty, D., Murphy, G. Immunoassays using radiolabels. In: Catty, D (Hrsg). *Antibodies Vol. II.* IRL Press Oxford (1989), 77–96.

Diehl, I. J., Kaufmann, M., Goerner R., Costa, S. D., Kaul, S., Bastert, G. Detection of tumor cells in bone marrow of patients with primary breast cancer: A prognostic factor for distant metastasis. *J. Clin. Oncol.* 10: 1534–1539 (1992).

Fisher, E. R., Redmond, C., Fisher, B., Bass, G. Pathologic findings from the National Surgical Adjuvant Breast and Bowel Projects (BSABP). Prognostic discriminants for 8-year survival for node-negative invasive breast cancer patients. *Cancer* 65: 2121–2128 (1990).

Günthert, U., Hofmann, M., Rudy, W., Reber, S., Zöller, M., Haußmann, I., Matzku, S., Wenzel, A., Ponta, H., and Herrlich, P. A new variant of glycoprotein CD44 confers metastatic potential to rat carcinoma cells. *Cell* 65: 13–24 (1991).

Heider, K.-H., Hofmann, M., Horst, E., van den Berg, F., Ponta, H., Herrlich, P., and Pals, S. T. A human homologue of the rat metastasis-associated variant of CD44 is expressed in colorectal carcinomas and adenomatous polyps. *J. Cell Biol.* 120: 227–233 (1993).

Hofmann, M., Rudy, W., Zöller, M., Tölg, C., Ponta, H., Herrlich P., and Günthert, U. CD44 splice variants confer metastatic behavior in rats: homologous sequences are expressed in human tumor cell lines. *Cancer Res.* 51: 5292–5297 (1991).

Jass, J. R. A classification of gastric dysplasia. *Histopath.* 7: 181–193 (1983).

Jida, F., and Kusama, J. Gastric and intestinal metaplasia. Significance of type of intestinal metaplasia upon development of gastric carcinoma. *Cancer* 50: 2854–2858 (1982).

Kato, Y., Kiagawa T., Nakamura, K., and Sugano, H. Changes in the histologic types of gastric carcinoma in Japan. *Cancer* 48: 2084–2087 (1981).

Kearney, J. F., Radbruch A., Liesegang B., Rajewski K. A new mouse myeloma cell line that has lost imunoglobulin expression but permits construction of antibody-secreting hybrid cell lines. *J. Immunol.* 123: 1548 (1979).

Köhler, G., Milstein, C. Continuous culture of fused cells secreting antibody of predefined specificity. *Nature* 265: 495 (1975)

Koopman, G., Heider, K.-H., Horts, E., Adolf, G. R., van den Berg, F., Ponta, H., Herrlich, P., Pals, S. T. Activated human lymphocytes and aggressive Non-Hodgkin's lymphomas express a homologue of the rat metastasis-associated variant of CD44. *J. Exp. Med.* 177: 897–904 (1993).

Laemmli, U. Cleavage of structural proteins during the assembly of the head of bacteriophage T4. *Nature* 227: 680–685 (1970).

Lauren P. The two histological main types of gastric carcinoma: diffuse and so-called intestinal-type carcinoma. *Acta Path. Microbiol. Scand.* 64: 31–49 (1965).

Mackay, C. R., Terpe, H.-J., Stauder, R., Marston, W. L., Stark, H., Günthert U. Expression and modulation of CD44 variant isoforms in humans. *J. Cell Biol.* 124: 71–82 (1994).

Mayer, B., Jauch, K. W., Gunthert, U., Figdor, C. G., Schildberg, F. W., Funke, I., Johnson, J. P. De-novo expression of CD44 and survival in gastric cancer. *Lancet* 342: 1019–1022 (1993).

Nomura, A., Stemmermann, G. N. Chyon, P. H., Kato, I., Perez-Perez, G. I. and Blaser, H. J. *Helicobacter pylori* infection and gastric carcinoma among Japanese americans in Hawaii. *New Engl. J. Med.* 325: 1132–1136 (1991).

Partk, R. C., Thigpen, J. T. Chemotherapy in advanced and recurrent cervical cancer. *Cancer* 71: 1446–1450 (1993).

Parsonnet, J., Friedman, G. D., Vandersteen, D. F., Chang, Y., Vogelman, J. H., Orentreich, N., and Sikley, R. K. *Helicobacter pylori* infection and the risk of gastric carcinoma. *New Engl. J. Med.* 325: 1127–1131 (1991).

Perez, C. A., Breaux, S., Madoo-Jones, H., Bedwinek, J. M., Camel, H. M., Purdy, J. A., Walz, B. J. Radiation therapy alone in the treatment of carcinoma of uterine Zervix. *Cancer* 51: 1393–1402 (1983).

Petterson, F. Annual report on results of treatment in gynecologic cancer. *FIGO Cancer Comitees*: Vol. 20 (1988).

Piper, D. W. Stomach cancer. In: "Geneva: International Union Against Cancer". *UICC Technical Report Series* Vol. 34 (1978).

Sambrook, J., Fritsch E. E., Maniatis I., *Molecular cloning.* Cold Spring Harbor Laboratory Press, Cold Spring Harbor (1989).

Screaton, G. R., Bell, M. V., Jackson, D. G., Cornelis, F. B., Gerth, U., and Bell, J. I. Genomic structure of DNA encoding the lymphocyte homing receptor CD44 reveals at least 12 alternatively spliced exons. *Proc. Natl. Acad. Sci. U.S.A.* 89: 12160–12164 (1992).

Sipponen, P., Kekki, M., and Surala, M. Atrophic chronic gastritis and intestinal metaplasia in gastric carcinoma. Comparison with a representative population sample. *Cancer* 52: 1062–1068 (1983).

Siurala, M., Lehtola, J., and Ihamäki, T. Atrophic gastric and its sequelae. Results of 15–23 years follow-up. *Scand. J. Gastroenterol.* 1: 40–48 (1974).

Smith, D. B., Johnson, K. S. Single-step purification of polypeptides expressed in *Escherichia coli* as fusions with glutathione S-transferase. *Gene* 67: 31 (1988).

Stamenkovic, I., Amiot, M., Pesando, J. M., and Seed, B. A lymphocyte molecule implicated in lymph node homing is a member of the cartilage link protein family. *Cell* 56: 1057–1062 (1989).

Strickland, R. G., and Mackay, I. R. A reappraisal of the nature and significance of chronic atrophic gastritis. *Dig. Dis. Sci.* 18: 426–440 (1973).

Tölg, C., Hofmann, M., Herrlich, P., and Ponta, H. Splicing choice from ten variant exons establishes CD44 variability. *Nucleic Acids. Res.* 21: 1225–1229 (1993).

Thomas, G. D., Dykes, P. W., Bradwell, A. R. Antibodies for tumour immunodetection and methods for antibody radiolabeling. In: Catty, D. (Hrsg.). *Antibodie Vol.* II. IRL Press Oxford, 223–244 (1989).

We claim:

1. A process for detecting a product of the combined expression of variable exons v7 and v8 of a gene encoding CD44, comprising:

(a) obtaining a human tissue sample;

(b) contacting the tissue sample with an antibody, wherein the antibody binds an epitope on CD44 that is encoded by exons v7 and v8 together, the epitope being contained in SEQ. ID. NO: 9; and (c) detecting the antibody bound to the tissue sample.

2. The process according to claim 1, wherein the human tissue sample is a tissue section.

3. An antibody that binds an epitope on CD44 that is encoded by exons v7 and v8 together, the epitope being contained in SEQ ID NO: 9.

4. The antibody according to claim 3, wherein the antibody is a monoclonal antibody.

5. The antibody according to claim 4, wherein the antibody is selected from the group consisting of an Fab fragment, an F(ab')$_2$ fragment, a recombinantly produced single-chain antibody (scFv), and a humanized antibody.

6. The antibody according to claim 4, wherein the antibody is VFF-17.

7. The antibody according to claim 3, wherein the antibody is purified.

* * * * *

SEQUENCE LISTING (1) GENERAL INFORMATION:

(iii) NUMBER OF SEQUENCES: 12

(2) INFORMATION FOR SEQ ID NO: 1:

(i) SEQUENCE CHARACTERISTICS:
        (A) LENGTH: 120 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:3..119

(ix) FEATURE:
        (A) NAME/KEY: exon
        (B) LOCATION:1..120

(xi) SEQUENCE DESCRIPTION: SEQ ID NO: 1:

```
CA GAT GTA GAC AGA AAT GGC ACC ACT GCT TAT GAA GGA AAC TGG AAC         47
   Asp Val Asp Arg Asn Gly Thr Thr Ala Tyr Glu Gly Asn Trp Asn
    1               5                  10                  15

CCA GAA GCA CAC CCT CCC CTC ATT CAC CAT GAG CAT CAT GAG GAA GAA        95
Pro Glu Ala His Pro Pro Leu Ile His His Glu His His Glu Glu Glu
                20                  25                  30

GAG ACC CCA CAT TCT ACA AGC ACA A                                     120
Glu Thr Pro His Ser Thr Ser Thr
            35
```

(2) INFORMATION FOR SEQ ID NO: 2:

(i) SEQUENCE CHARACTERISTICS:
        (A) LENGTH: 39 amino acids
        (B) TYPE: amino acid
        (D) TOPOLOGY: linear (ii) MOLECULE TYPE: protein (xi) SEQUENCE DESCRIPTION: SEQ ID NO: 2:

```
Asp Val Asp Arg Asn Gly Thr Thr Ala Tyr Glu Gly Asn Trp Asn Pro
 1               5                  10                  15

Glu Ala His Pro Pro Leu Ile His His Glu His His Glu Glu Glu
            20                  25                  30

Thr Pro His Ser Thr Ser Thr
            35
```

(2) INFORMATION FOR SEQ ID NO:3:

(i) SEQUENCE CHARACTERISTICS:
        (A) LENGTH: 129 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:3..128

(ix) FEATURE:
        (A) NAME/KEY: exon
        (B) LOCATION:1..129

(xi) SEQUENCE DESCRIPTION: SEQ ID NO: 3:

```
TC CAG GCA ACT CCT AGT AGT ACA ACG GAA GAA ACA GCT ACC CAG AAG         47
   Gln Ala Thr Pro Ser Ser Thr Thr Glu Glu Thr Ala Thr Gln Lys
   40                  45                  50
```

```
GAA CAG TGG TTT GGC AAC AGA TGG CAT GAG GGA TAT CGC CAA ACA CCC      95
Glu Gln Trp Phe Gly Asn Arg Trp His Glu Gly Tyr Arg Gln Thr Pro
 55                  60                  65                  70

AGA GAA GAC TCC CAT TCG ACA ACA GGG ACA GCT G                        129
Arg Glu Asp Ser His Ser Thr Thr Gly Thr Ala
             75                  80
```

(2) INFORMATION FOR SEQ ID NO: 4:

(i) SEQUENCE CHARACTERISTICS:
        (A) LENGTH: 42 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 4:

```
Gln Ala Thr Pro Ser Ser Thr Thr Glu Glu Thr Ala Thr Gln Lys Glu
 1                5                  10                  15

Gln Trp Phe Gly Asn Arg Trp His Glu Gly Tyr Arg Gln Thr Pro Arg
             20                  25                  30

Glu Asp Ser His Ser Thr Thr Gly Thr Ala
         35                  40
```

(2) INFORMATION FOR SEQ ID NO: 5:

(i) SEQUENCE CHARACTERISTICS:
        (A) LENGTH: 132 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:3..131

(ix) FEATURE:
        (A) NAME/KEY: exon
        (B) LOCATION:1..132

(xi) SEQUENCE DESCRIPTION: SEQ ID NO: 5:

```
CA GCC TCA GCT CAT ACC AGC CAT CCA ATG CAA GGA AGG ACA ACA CCA       47
   Ala Ser Ala His Thr Ser His Pro Met Gln Gly Arg Thr Thr Pro
                45                  50                  55

AGC CCA GAG GAC AGT TCC TGG ACT GAT TTC TTC AAC CCA ATC TCA CAC      95
Ser Pro Glu Asp Ser Ser Trp Thr Asp Phe Phe Asn Pro Ile Ser His
             60                  65                  70

CCC ATG GGA CGA GGT CAT CAA GCA GGA AGA AGG ATG G                    132
Pro Met Gly Arg Gly His Gln Ala Gly Arg Arg Met
         75                  80                  85
```

(2) INFORMATION FOR SEQ ID NO: 6:

(i) SEQUENCE CHARACTERISTICS:
        (A) LENGTH: 44 amino acids
        (B) TYPE: amino acid
        (D) TOPOLOGY: linear (ii) MOLECULE TYPE: protein (xi) SEQUENCE DESCRIPTION: SEQ ID NO: 6:

```
Ala Ser Ala His Thr Ser His Pro Met Gln Gly Arg Thr Thr Pro Ser
 1                5                  10                  15

Pro Glu Asp Ser Ser Trp Thr Asp Phe Phe Asn Pro Ile Ser His Pro
             20                  25                  30
```

```
Met Gly Arg Gly His Gln Ala Gly Arg Arg Met Asp
        35                  40
```

(2) INFORMATION FOR SEQ ID NO: 7:

(i) SEQUENCE CHARACTERISTICS:
        (A) LENGTH: 102 base pairs
        (B) TYPE: nucleic acid
        (C) STRANDEDNESS: double
        (D) TOPOLOGY: linear (ii) MOLECULE TYPE: DNA (genomic)

(ix) FEATURE:
        (A) NAME/KEY: CDS
        (B) LOCATION:3..101

(ix) FEATURE:
        (A) NAME/KEY: exon
        (B) LOCATION:1..102

(xi) SEQUENCE DESCRIPTION: SEQ ID NO: 7:

```
AT ATG GAC TCC AGT CAT AGT ACA ACG CTT CAG CCT ACT GCA AAT CCA        47
   Met Asp Ser Ser His Ser Thr Thr Leu Gln Pro Thr Ala Asn Pro
        45                  50                  55

AAC ACA GGT TTG GTG GAA GAT TTG GAC AGG ACA GGA CCT CTT TCA ATG        95
Asn Thr Gly Leu Val Glu Asp Leu Asp Arg Thr Gly Pro Leu Ser Met
    60                  65                  70

ACA ACG C                                                             102
Thr Thr
 75
```

(2) INFORMATION FOR SEQ ID NO:8:

(i) SEQUENCE CHARACTERISTICS:
        (A) LENGTH: 34 amino acids
        (B) TYPE: amino acid
        (D) TOPOLOGY: linear (ii) MOLECULE TYPE: protein (xi) SEQUENCE DESCRIPTION: SEQ ID NO:8:

```
Met Asp Ser Ser His Ser Thr Thr Leu Gln Pro Thr Ala Asn Pro Asn
 1               5                  10                  15

Thr Gly Leu Val Glu Asp Leu Asp Arg Thr Gly Pro Leu Ser Met Thr
            20                  25                  30

Thr Gln
```

(2) INFORMATION FOR SEQ ID NO: 9:

(i) SEQUENCE CHARACTERISTICS:
        (A) LENGTH: 78 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 9:

```
Ala Ser Ala His Thr Ser His Pro Met Gln Gly Arg Thr Thr Pro Ser
 1               5                  10                  15

Pro Glu Asp Ser Ser Trp Thr Asp Phe Phe Asn Pro Ile Ser His Pro
            20                  25                  30

Met Gly Arg Gly His Gln Ala Gly Arg Arg Met Asp Met Asp Ser Ser
            35                  40                  45

His Ser Thr Thr Leu Gln Pro Thr Ala Asn Pro Asn Thr Gly Leu Val
```

```
                    50                   55                  60
Glu Asp Leu Asp Arg Thr Gly Pro Leu Ser Met Thr Thr Gln
65                      70                  75

(2) INFORMATION FOR SEQ ID NO: 10:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 10:

Gln Trp Phe Gly Asn Arg Trp His Glu Gly Tyr Arg Gln Thr
1               5                   10

(2) INFORMATION FOR SEQ ID NO: 11:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 11:

CAGGCTGGGA GCCAAATGAA GAAAATG                                           27

(2) INFORMATION FOR SEQ ID NO: 12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA to mRNA (xi) SEQUENCE DESCRIPTION: SEQ ID NO: 12:

TGATAAGGAA CGATTGACAT TAGAGTTGGA                                        30
```